United States Patent
Huang

(10) Patent No.: US 10,870,873 B2
(45) Date of Patent: *Dec. 22, 2020

(54) METHOD OF USING CARBOHYDRATE ESTERS AS INDUCERS FOR GENE EXPRESSION

(71) Applicant: Qingdao Vland Biotech Group Co., Ltd., Qingdao (CN)

(72) Inventor: Tom Tao Huang, Fremont, CA (US)

(73) Assignee: Qingdao Vland Biotech Group Co., Ltd., Qingdao (CN)

( * ) Notice: Subject to any disclaimer, the term of this patent is extended or adjusted under 35 U.S.C. 154(b) by 150 days.

This patent is subject to a terminal disclaimer.

(21) Appl. No.: 16/020,429

(22) Filed: Jun. 27, 2018

(65) Prior Publication Data

US 2018/0327804 A1 Nov. 15, 2018

Related U.S. Application Data

(63) Continuation of application No. 14/414,957, filed as application No. PCT/US2013/051147 on Jul. 18, 2013, now Pat. No. 10,059,973.

(60) Provisional application No. 61/673,997, filed on Jul. 20, 2012, provisional application No. 61/746,120, filed on Dec. 27, 2012.

(51) Int. Cl.

| | | |
|---|---|---|
| *C12P 21/00* | (2006.01) |
| *C07H 13/04* | (2006.01) |
| *C12P 19/12* | (2006.01) |
| *C12P 19/44* | (2006.01) |
| *C12P 21/02* | (2006.01) |
| *C12N 1/14* | (2006.01) |
| *C12N 1/38* | (2006.01) |
| *C12N 9/26* | (2006.01) |
| *C12N 9/42* | (2006.01) |
| *C12N 15/80* | (2006.01) |
| *C07K 14/475* | (2006.01) |
| *C07K 14/575* | (2006.01) |
| *C07K 16/00* | (2006.01) |

(52) U.S. Cl.
CPC .......... *C12P 21/005* (2013.01); *C07H 13/04* (2013.01); *C07K 14/475* (2013.01); *C07K 14/575* (2013.01); *C07K 16/00* (2013.01); *C12N 1/14* (2013.01); *C12N 1/38* (2013.01); *C12N 9/2408* (2013.01); *C12N 9/2411* (2013.01); *C12N 9/2434* (2013.01); *C12N 9/2437* (2013.01); *C12N 15/80* (2013.01); *C12P 19/12* (2013.01); *C12P 19/44* (2013.01); *C12P 21/02* (2013.01)

(58) Field of Classification Search
CPC .... C07H 13/04; C07K 14/475; C07K 14/575; C07K 16/00; C12N 15/80; C12N 1/14; C12N 1/38; C12N 9/2408; C12N 9/2411; C12N 9/2434; C12N 9/2437; C12N 9/2402; C12P 19/12; C12P 19/44; C12P 21/005; C12P 21/02; C12P 19/02; C12P 19/14; C12P 7/06; C12Y 101/03004; C12Y 302/01008; C12Y 302/01021; C12Y 302/01091; C12Y 503/01005; Y02E 50/17

See application file for complete search history.

(56) References Cited

U.S. PATENT DOCUMENTS

| | | | |
|---|---|---|---|
| 4,818,816 A | 4/1989 | Petitou |
| 5,767,255 A | 6/1998 | Wullbrandt |
| 5,981,497 A | 11/1999 | Maingault |
| 6,433,152 B1 | 8/2002 | Lang |
| 8,148,108 B2 | 4/2012 | Ju |
| 8,323,931 B2 | 12/2012 | Gudynaite-Savitvh |
| 9,012,194 B2 | 4/2015 | Gross |
| 2009/0008325 A1 | 1/2009 | Ju |
| 2010/0009408 A1 | 1/2010 | England |
| 2011/0237531 A1 | 9/2011 | Yanagisawa |

FOREIGN PATENT DOCUMENTS

WO 2013/003291 1/2013

OTHER PUBLICATIONS

Asmer, et al. "Microbial production, structure elucidation and bioconversion of sophorose lipids." Journal of the American Oil Chemists' Society 65, No. 9 (1988): 1460-1466.
Carr, et al. "Enzyme-catalyzed regioselective transesterification of peracylated sophorolipids." Tetrahedron 59, No. 39 (2003): 7713-7724.
Davila, et al. "Identification and determination of individual sophorolipids in fermentation products by gradient elution high-performance liquid chromatography with evaporative light-scattering detection." Journal of Chromatography A 648, No. 1 (1993): 139-149.
Davila, et al. "Sophorose lipid production from lipidic precursors: predictive evaluation of industrial substrates." Journal of industrial microbiology 13, No. 4 (1994): 249-257.
Esterbauer, et al. "Production of Trichoderma cellulase in laboratory and pilot scale." Bioresource Technology 36, No. 1 (1991): 51-65.
Fleurackers, "On the use of waste frying oil in the synthesis of sophorolipids." European journal of lipid science and technology 108, No. 1 (2006): 5-12.

(Continued)

*Primary Examiner* — Deborah K Ware
(74) *Attorney, Agent, or Firm* — Kilpatrick Townsend & Stockton LLP

(57) ABSTRACT

The invention provides novel carbohydrate esters, in particular disaccharide esters, and the methods of their preparation. These compounds find use as microbial media components for the induction of gene expression in microbial fermentation processes.

13 Claims, 3 Drawing Sheets

(56) References Cited

OTHER PUBLICATIONS

Huang, et al., "New-to-nature sophorose analog: a potent inducer for gene expression in Trichoderma reesei." Enzyme and microbial technology 85 (2016): 44-50.
Kubicek, et al. "Metabolic engineering strategies for the improvement of cellulase production by Hypocrea jecorina." Biotechnology for biofuels 2, No. 1 (2009): 19.
Kurtzman, et al. "Production of sophorolipid biosurfactants by multiple species of the *Starmerella* (*Candida*) *bombicola* yeast Glade." FEMS microbiology letters 311, No. 2 (2010): 140-146.
Liu, et al. "Improved heterologous gene expression in Trichoderma reesei by cellobiohydrolase I gene (cbh1) promoter optimization." Acta biochimica et biophysica Sinica 40, No. 2 (2008): 158-165.
Lo, et al. "Sophorolipids-induced cellulase production in cocultures of Hypocrea jecorina Rut C30 and Candida bombicola." Enzyme and Microbial Technology 44, No. 2 (2009): 107-111.
Mandels, et al. "Sophorose as an inducer of cellulase in Trichoderma viride." Journal of Bacteriology 83, No. 2 (1962): 400-408.
Messner, et al., "Carbon source control of cellobiohydrolase I and II formation by Trichoderma reesei." Applied and environmental microbiology 57, No. 3 (1991): 630-635.
Penfold, et al. "Solution self-assembly of the sophorolipid biosurfactant and its mixture with anionic surfactant sodium dodecyl benzene sulfonate." Langmuir 27, No. 14 (2011): 8867-8877.
Ratsep, et al. "Identification and quantification of sophorolipid analogs using ultra-fast liquid chromatography—mass spectrometry." Journal of microbiological methods 78, No. 3 (2009): 354-356.
Rau, et al. "Sophorolipids: a source for novel compounds." Industrial Crops and Products 13, No. 2 (2001): 85-92.
Singh, et al. "Regioselective enzyme-catalyzed synthesis of sophorolipid esters, amides, and multifunctional monomers." The Journal of organic chemistry 68, No. 14 (2003): 5466-5477.
Thompson, et al. "Acid reversion products from D-glucose." Journal of the American Chemical Society 76, No. 5 (1954): 1309-1311.
Van Bogaert, et al. "Microbial synthesis of sophorolipids." Process Biochemistry 46, No. 4 (2011): 821-833.

A

B

METHOD OF USING CARBOHYDRATE ESTERS AS INDUCERS FOR GENE EXPRESSION

CROSS-REFERENCE TO RELATED APPLICATIONS

This application is a Continuation of U.S. application Ser. No. 14/414,957, filed Jan. 15, 2015, which is a 371 U.S. National Phase Application of PCT/US2013/051147, international filing date Jul. 18, 2013, which claims the benefit of U.S. Provisional Applications Ser. No. 61/673,997, filed Jul. 20, 2012 and 61/746,120, filed Dec. 27, 2012, the contents of which are incorporated in their entirety.

STATEMENT AS TO FEDERALLY SPONSORED RESEARCH

The U.S. government owns certain rights in the present application pursuant to grant number #2012-33610-19542 from the United States Department of Agriculture.

TECHNICAL FIELD

The present invention relates to chemical compounds and methods of their preparation for use as inducers of gene expression in cell culturing. More particularly, this invention is related to the development of low cost and highly efficient protein inducers that significantly lower the manufacturing cost for enzyme manufacturers.

BACKGROUND OF THE INVENTION

Cheap and readily available industrial enzymes are the key drivers behind the industrial biotechnology revolution where chemicals and energy fuels are increasingly being produced biologically using renewable resources. In contrast to high margin enzymes or other proteins used for therapeutic and diagnostic purposes, industrial enzymes typically have lower margins and are manufactured in large quantities with limited downstream processing after fermentation. For the industrial enzyme market, the production costs are of critical importance to commercial success. In order to fulfill the increasing demand for cheaper and readily available enzymes for the renewable chemicals and energy industries, there is an urgent need for more efficient and cost-effective production processes.

Major industrial enzyme manufacturers all have significant production capacities devoted to fungal fermentation, in particular using filamentous fungi such as *Aspergillus* spp, *Penicillium* spp, *Trichoderma* spp., *Chrysosporium lucknowense* (C1) and *Myceliophthora thermophila* (reclassified)), to make a range of enzyme products used in the textile, detergent, food and feed, and the nascent biofuels industries (Sharma et al., *World J. of Microbiol. and Biotech.*, 25(12): 2083-2094 (2009); Visser et al., *Industrial Biotech.*, 7(3): 214-223 (2011)).

Commercial production of a protein of interest in *Aspergillus* and *Trichoderma* typically requires an inducer compound that activates the transcriptional switch under a strong native promoter driving a gene of interest expressing a targeted enzyme or protein. Insoluble substrates such as starch and cellulose are typically used in laboratory scale to induce protein expression in *Aspergillus* and *Trichoderma*, respectively. Their implementation at industrial scale, however, is hampered by poor substrate consistency and materials and handling issues encountered at large scale such as sterilization, feeding, mixing, and viscosity issues. Consequently, highly efficient soluble inducers are more preferred in the commercial production of enzymes and other proteins.

Maltose, isomaltose, and maltodextrins are commonly used as soluble inducers for the induction of alpha-amylase and glucoamylase enzymes in *Aspergillus* spp. (Barton et al., *J. Bacteriol.*, b(3):771-777 (1972)), while sophorose, cellobiose, and lactose are three effective soluble inducers widely used in the industry for enzyme production in *Trichoderma* spp. (Kubicek et al., *Biotech. Biofuels,* 2:19 (2009)). Sophorose, a beta 1, 2-disaccharide, is considered to be the most powerful inducer of the cellulase gene promoter in *Trichoderma reesei*, being 2500 times as active as cellobiose (Mandels et al., *J. Bacteriol.,* 83(2):400-408 (1962)). These respective soluble inducers are all metabolized by *Aspergillus* or *Trichoderma* before, during, or after induction. Therefore, they are not considered as gratuitous inducers, thus requiring them to be continually supplied during the fermentation in order to achieve optimum induction.

In industrial enzyme production through submerged fermentation, soluble inducers are typically supplied to the fermenter in a fed batch either alone or supplemented with alternative carbon sources such as glucose in a carbon-limited fashion. Due to the inducers being non-gratuitous, the induction process, if not fully optimized, will typically cause catabolic repression that significantly lowers the productivity, along with unnecessary growth that significantly lowers the yield. Thus, there exists a need in the art for a stronger, gratuitous, or nearly gratuitous inducer that decouples induction from unintended repression, growth, or other physiological functions, allowing more rigorous process optimization to significantly improve productivity and yield than is currently possible. A more powerful inducer can also be easily used to supply the induction needs of cheaper and non-inductive feedstocks as well as to enhance the induction of conventional inducers such as lactose, cellulose, maltodextrins, or cheaper alternatives such as starch and cellulose hydrolysates, and also in alternative production processes such as solid-phase fermentations.

Because carbohydrate-based inducers are both inducers and repressors for protein expression, methods to enhance the induction power by modifying the inducer to slow its uptake or metabolization are known. Hydrolysis products of cellobiose octaacetate, although not characterized, are known to carry superior induction power than cellobiose (Mandels and Reese, *J. Bacteriol.,* 79(6):816-826 (1960)). Sucrose monopalmitate induced a sucrase yield that is 80 times that of sucrose in *Pullularia pullulans* (Reese et al., *J. Bacteriol.,* 100(3):1151-1154 (1969)). Similarly, acetyl cellobioses were more effective than glucose or cellobiose at inducing cellulase in *Penicillium purpurogenum*, with mono-O-acetyl cellobiose being the most active inducer tested (Suto et al., *J. Ferment. Bioengin.*, 72(5):352-357 (1991)). A recent filing by the inventor (International Application No.: WO 2013/003291) disclosed a novel class of sophorose esters derived from dilute acid treatment of natural sophorolipid that is at least a 30 times more powerful inducer than sophorose itself.

BRIEF SUMMARY OF THE INVENTION

In one aspect, the present invention provides a method for producing a protein of interest comprising providing a fermentation host and culturing the fermentation host with a carbon source and one or more compounds selected from the group consisting of:

1) formula I

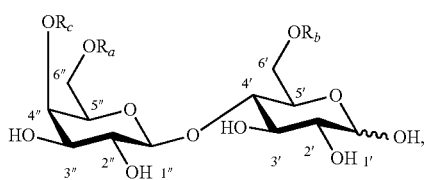

2) formula II

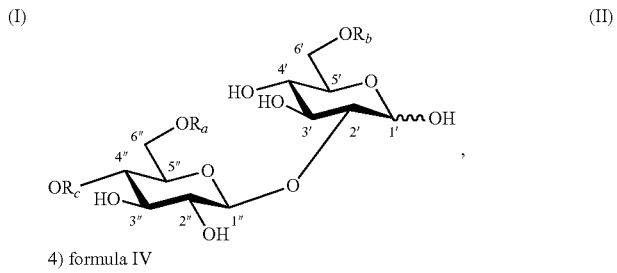

3) formula III

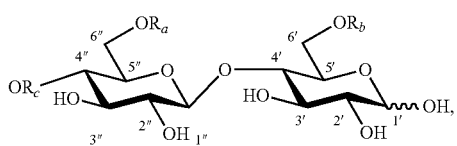

4) formula IV 5) formula V

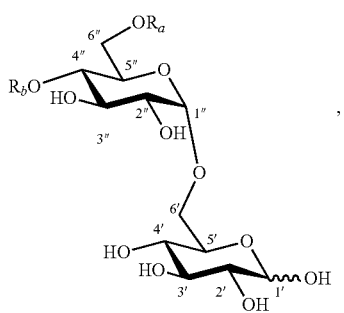

6) formula VI 7) formula VII

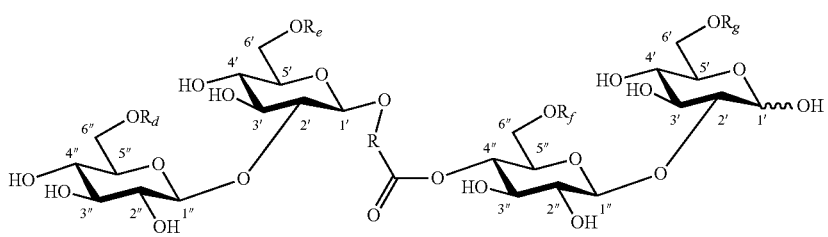

where $R_a$ is H or C(O)R;
$R_b$ is H or C(O)R;
$R_c$ is H or C(O)R;
$R_d$ is H or C(O)CH$_3$;
$R_e$ is H or C(O)CH$_3$;
$R_f$ is H or C(O)CH$_3$;
$R_g$ is H or C(O)CH$_3$; and
R is an aliphatic moiety, with the proviso that in formula (II), $R_c$ is H when $R_a$ is H or C(O)CH$_3$ and $R_b$ is H or C(O)CH$_3$, wherein the fermentation host is cultured under conditions sufficient to produce a protein of interest. In one embodiment, the protein of interest is cellulase or amylase. In another embodiment, the protein of interest is a homologous or heterologous protein. In a further embodiment, the homologous or heterologous protein is an enzyme, a hormone, a growth factor, a cytokine or an antibody. In one embodiment, the fermentation host is capable of producing cellulase or amylase. In another embodiment, the fermentation host is a filamentous fungus or bacteria or other hosts selected from the genus group consisting of *Trichoderma*, *Humicola*, *Pleurotus*, *Fusarium*, *Aspergillus*, *Streptomyces*, *Thermomonospora*, *Bacillus*, *Cellulomonas*, *Penicillium*, Basidiomycete, Chrysoporium, *Pestalotiopsis*, *Neurospora*, *Cephalosporium*, Achlya, Podospora, Endothia, *Mucor*, *Cochliobolus*, *Myceliopthora*, *Talaromyces*, and Pyricularia. In a further embodiment, the fermentation host is the filamentous fungus *Trichoderma reesei* or *Aspergillus niger*. In one embodiment, the fermentation host is grown in a liquid culture or on a solid substrate without free-flowing liquid. In another embodiment, the fermentation host has a promoter operably linked to a gene encoding a protein of interest. In a further embodiment, the promoter is a cellulase gene promoter or an amylase gene promoter. In another embodiment, the promoter is a cbh1 promoter or a glaA promoter or an amyA promoter. In one embodiment, the carbon source is biomass. In another embodiment, the biomass is glucose, sucrose, fructose, glycerol, lactose, cellulose, cellulose hydrolysate, starch, starch hydrolysate, maltose, or maltodextrin.

In another aspect, the compound of formula (I), (II), (III), (IV) and (V) is isolated from a crude product mixture from either a chemical or enzymatically catalyzed trans-esterification reaction. In one embodiment, the compounds of formula (VI) are isolated from formic acid treatment process of natural lactonic sophorolipid. In another embodiment, the compounds of formula (VII) are isolated from the culture of the yeast *Candida bombicola*. In another embodiment, R is an aliphatic moiety selected from unsubstituted $C_1$-$C_{24}$ alkyl, substituted $C_1$-$C_{24}$ alkyl, unsubstituted $C_2$-$C_{24}$ alkenyl, and substituted $C_2$-$C_{24}$ alkenyl. In a further embodiment, R is an aliphatic moiety selected from $C_1$-$C_{24}$ alkyl substituted with hydroxyl groups and $C_2$-$C_{24}$ alkenyl substituted with hydroxyl groups. In yet another embodiment, R is an aliphatic moiety selected from $C_1$-$C_{24}$ alkyl substituted with carboxyl groups and $C_2$-$C_{24}$ alkenyl substituted with carboxyl groups. In a further embodiment, R is an aliphatic moiety selected from $C_1$-$C_{24}$ alkyl substituted with aromatic groups and $C_2$-$C_{24}$ alkenyl substituted with aromatic groups. In another embodiment, the compound of formula (I), (II), (III), (IV), (V), (VI), and (VII) comprises:

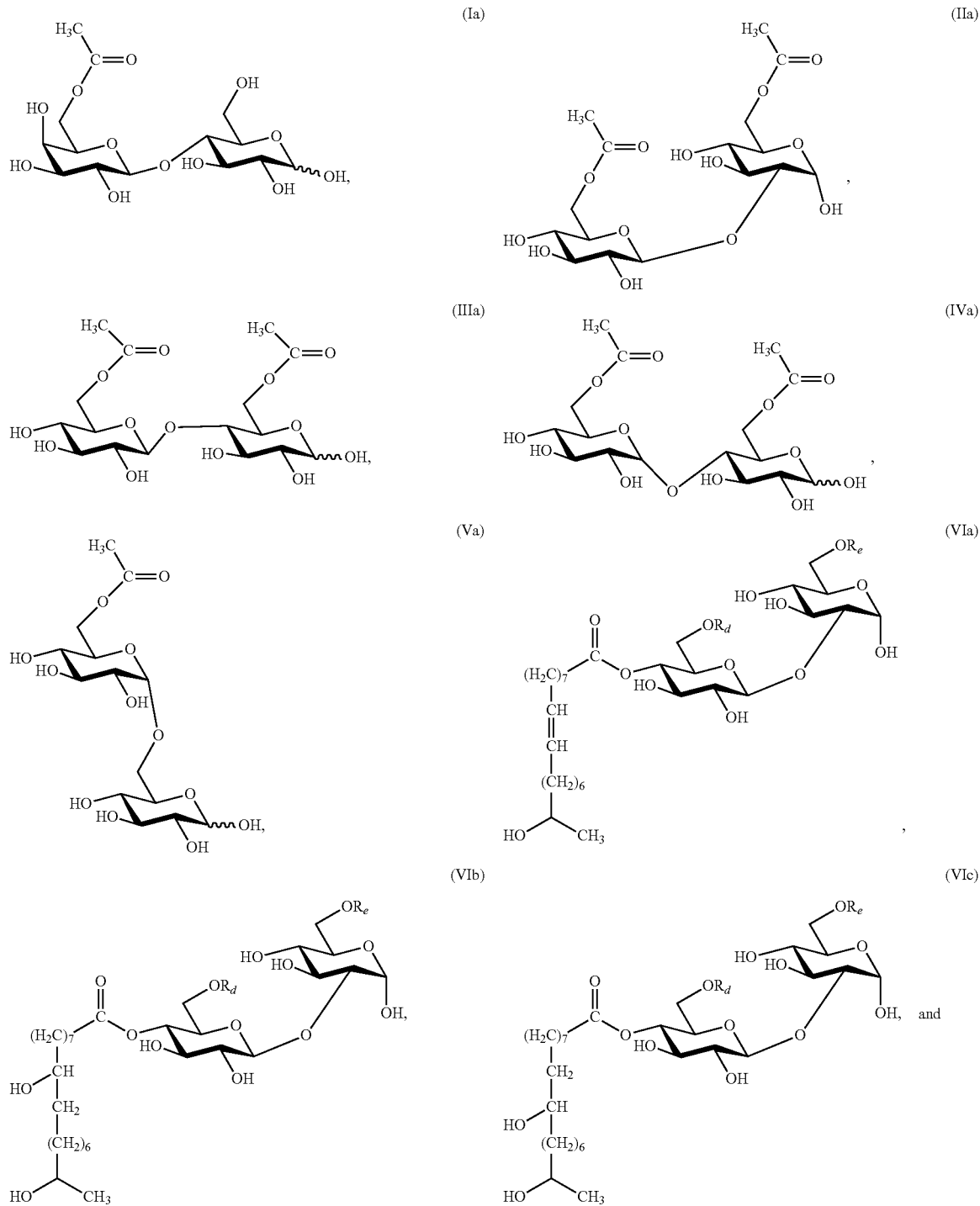

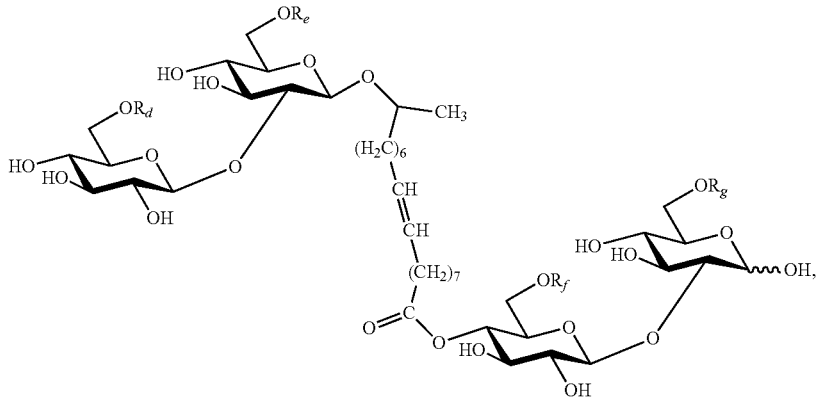
(VIIa)

where $R_d$ is H or $C(O)CH_3$;
$R_e$ is H or $C(O)CH_3$;
$R_f$ is H or $C(O)CH_3$;
and $R_g$ is H or $C(O)CH_3$.

In another aspect, the present invention provides a method for producing one or more compounds of formula (I), formula (II), formula (III), formula (IV) or formula (V) comprising providing a disaccharide; and contacting the disaccharide with a vinyl ester in the presence of a lipase enzyme in a solvent system. In one embodiment, the disaccharide comprises lactose, sophorose, cellobiose, maltose, or isomaltose. In another embodiment, the lipase enzyme comprises Novozyme 435, Lipozyme TL, Lipozyme RM, or Amano lipase PS. In a further embodiment, the vinyl ester comprises vinyl acetate, vinyl propionate, vinyl butyrate, vinyl cinnamate, vinyl methacrylate, vinyl oleate, vinyl linoleate, vinyl palmitate, or vinyl stearate. In another embodiment, the solvent system comprises a polar solvent mixed with tert-amyl alcohol, tert-butyl alcohol, tetrahydrofuran, acetone, methanol, or acetonitrile. In a further embodiment, the polar solvent comprises dimethyl sulfoxide (DMSO), pyridine, or dimethylformamide (DMF). In another embodiment the method further comprises heating to a temperature between 40° C. to 100° C. In yet another embodiment, the method further comprises vacuum distillation to remove the solvent system and isolating the product of interest.

In another aspect, the present invention provides a method for producing one or more compounds of formula (I), formula (II), formula (III), formula (IV) or formula (V) by an acid or base catalyzed trans-esterification reaction of an appropriate disaccharide with a suitable vinyl ester in a solvent system. In one embodiment, the base is potassium carbonate ($K_2CO_3$), sodium hydroxide (NaOH), or potassium hydroxide (KOH). In another embodiment, the acid is sulfuric acid ($H_2SO_4$) or hydrochloric acid (HCl). In a further embodiment, the vinyl ester comprises vinyl acetate, vinyl propionate, vinyl butyrate, vinyl cinnamate, vinyl methacrylate, vinyl oleate, vinyl linoleate, vinyl palmitate, or vinyl stearate. In another embodiment, the solvent system comprises a polar solvent such as dimethyl sulfoxide (DMSO), pyridine, or dimethylformamide (DMF).

In another aspect, the present invention provides a method for producing one or more compounds of formula (VI) comprising reacting natural lactonic sophorolipid with formic acid or acetic acid under substantially non-aqueous conditions and partially or completely removing formate or acetate esters formed. In one embodiment, a second acid catalyzes the reaction of the natural sophorolipid with formic acid or acetic acid. In another embodiment, the second acid comprises sulfuric acid ($H_2SO_4$) or hydrochloric acid (HCl). In a further embodiment, the natural sophorolipid is produced by a fermentation host. In another embodiment, the fermentation host is *Candida bombicola*. In one embodiment, the substantially non-aqueous conditions comprise a reaction mixture having a water content of no more than about 10%. Another embodiment further comprises the step of heating at a temperature between 40° C. to 120° C. before the step of partially or completely removing the formate or acetate esters formed. In a further embodiment, the removal of the formate esters comprises refluxing in acetic acid and methanol. In another embodiment, the removal of the acetate esters comprises treating with an acid or a base.

In another aspect, the present invention provides a method for producing one or more compounds of formula (VII) by a fermentation host. In one embodiment, the fermentation host is *Candida bombicola*. In another embodiment, the compounds of formula (VII) and (VIIa) are isolated from a crude mixture from a culture of *Candida bombicola*.

In another aspect, the present invention provides a method for producing sophorose comprising reacting natural sophorosides with formic acid under substantially non-aqueous conditions and completely removing formate esters formed, wherein a purified sophorose is obtained. In one embodiment, the natural sophorosides are steviosides, sophorolipids, and flavonoid sophorosides. In another embodiment the step of reacting natural sophorosides with formic acid step is catalyzed by a second acid. In one embodiment, the second acid comprises sulfuric acid ($H_2SO_4$) or hydrochloric acid (HCl). In a further embodiment, the substantially non-aqueous conditions comprise a reaction mixture having a water content of no more than about 10%. In another embodiment, the method further comprises the step of heating at a temperature between 40° C. to 120° C. before the step of completely removing the formate esters. In a further embodiment, the step of completely removing the formate esters comprises treating with a base in a solvent. In one embodiment, the base is sodium methoxide ($CH_3NaO$) or ammonia ($NH_3$) and the solvent is methanol or ethanol.

In another aspect, the present invention provides a compound having a structure of formula (II):

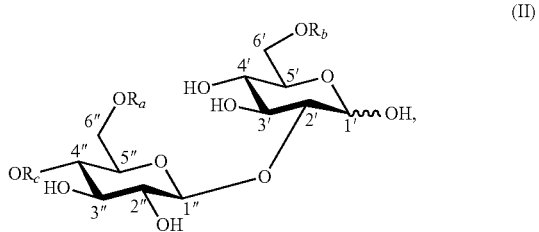

(II)

wherein:
$R_a$ is H or C(O)R;
$R_b$ is H or C(O)R;
$R_c$ is H or C(O)R; and
R is an aliphatic moiety, with the proviso that $R_c$ is H when $R_a$ is H or C(O)CH$_3$ and $R_b$ is H or C(O)CH$_3$. In one embodiment, R is selected from the group consisting of unsubstituted $C_1$-$C_{24}$ alkyl; $C_1$-$C_{24}$ alkyl substituted with hydroxyl, carboxyl or aromatic groups; unsubstituted $C_2$-$C_{24}$ alkenyl; and $C_2$-$C_{24}$ alkenyl substituted with hydroxyl, carboxyl or aromatic groups. In another embodiment, R is an aliphatic moiety selected from unsubstituted $C_1$-$C_{24}$ alkyl, substituted $C_1$-$C_{24}$ alkyl, unsubstituted $C_2$-$C_{24}$ alkenyl, and substituted $C_2$-$C_{24}$ alkenyl. In a further embodiment, R is an aliphatic moiety selected from $C_1$-$C_{24}$ alkyl substituted with hydroxyl groups and $C_2$-$C_{24}$ alkenyl substituted with hydroxyl groups. In another embodiment, R is an aliphatic moiety selected from $C_1$-$C_{24}$ alkyl substituted with carboxyl groups and $C_2$-$C_{24}$ alkenyl substituted with carboxyl groups. In a further embodiment, R is an aliphatic moiety selected from $C_1$-$C_{24}$ alkyl substituted with aromatic groups and $C_2$-$C_{24}$ alkenyl substituted with aromatic groups.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present invention relates to the chemical or biological modification of known carbohydrate inducers such as lactose, sophorose, and maltose in a cost effective manner that enhances their induction power in the production of industrially desirable proteins. The induction power of lactose, sophorose, and maltose is enhanced by several folds by modification to disaccharide esters, in particular as soluble monoesters, diesters, and triesters. Significantly improved yields of cellulase, amylase or other proteins under the control of a suitable promoter can be induced at higher yields than is currently possible. The present invention has the potential to significantly impact current enzyme production economics by improving both productivity and operations logistic in the manufacturing plant.

The present invention also relates to a more effective method to produce novel and highly inductive sophorose esters from natural lactonic sophorolipid and the use of a novel, sophorolipid dimer ester compound as a highly potent inducer. Due to the ease of preparation of this new class of compounds, ready-to-use and industrially applicable inducers can be produced, which are also highly efficient and cost-effective. Furthermore, a more effective method of producing sophorose from natural sophorosides such as stevioside and sophorolipid is also described.

Carbohydrate Esters

Figure 1:
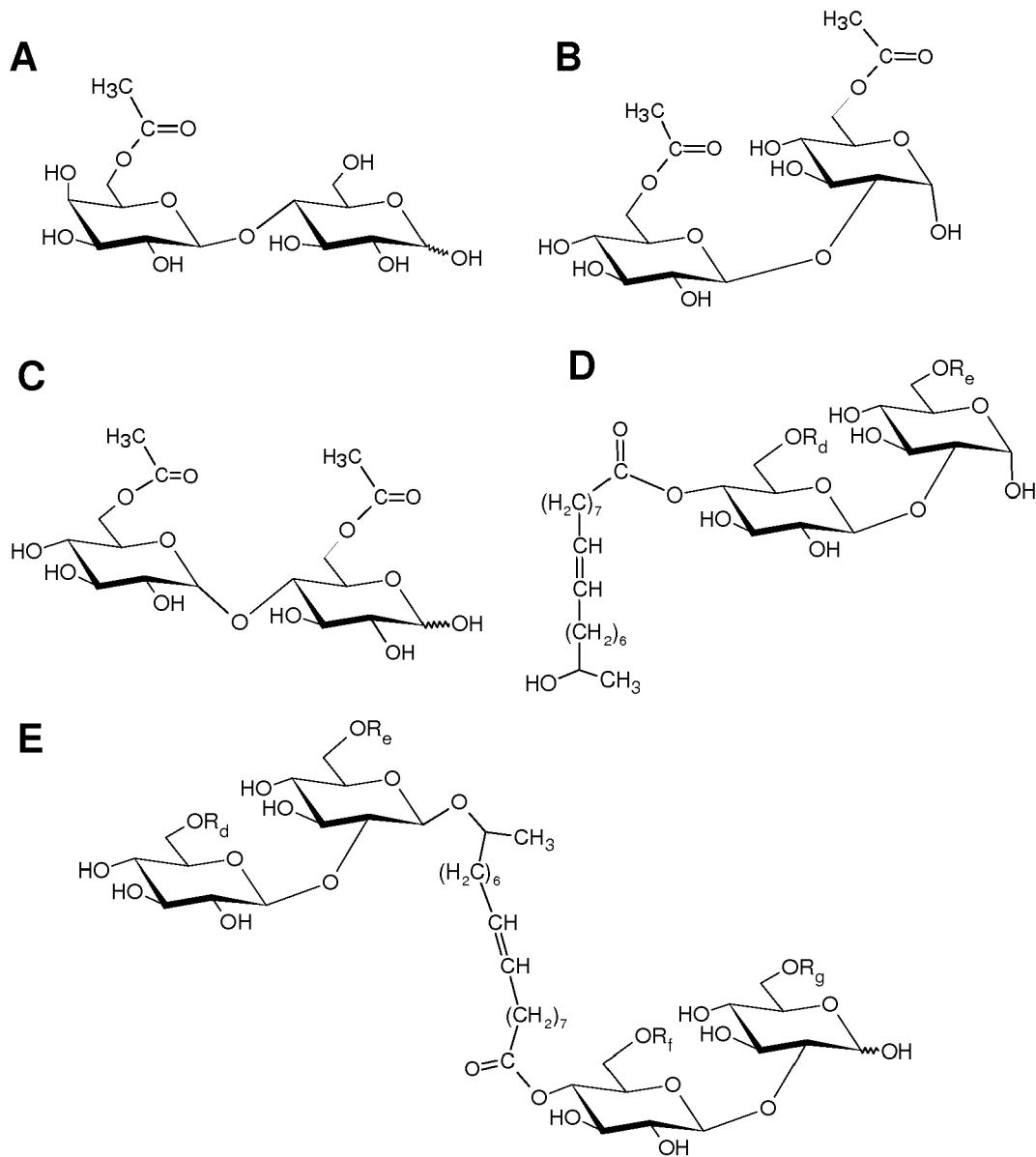
FIG. 1 shows examples of carbohydrate esters for use as inducers for gene expression: (A) 6″ acetylated lactose monoester; (B) 6′ and 6″ acetylated alpha-sophorose diester; (C) 6′ and 6″acetylated maltose diester; (D) a deacetylated or 6′ and/or 6″ acetylated alpha-sophorose ester esterified at C-4″ position with an 18-carbon monounsaturated fatty alcohol hydroxylated at the C-17 position of the fatty alcohol chain; and (E) a deacetylated or 6′ and/or 6″ acetylated dimeric sophorolipid ester. In this figure, $R_d$=H or C(O)CH$_3$; $R_e$=H or C(O)CH$_3$; $R_f$=H or C(O)CH$_3$; and $R_g$=H or C(O)CH$_3$.

Lactose, sophorose, cellobiose, maltose, or isomaltose monoester or diester compounds are produced by a trans-esterification reaction of unmodified disaccharide and a vinyl ester according to the method of the present invention. FIGS. 1A through 1C depict three exemplary disaccharide monoacetates or diacetates that can be produced chemically or enzymatically from the trans-esterification reaction of a disaccharide and a vinyl acetate according to the method of the invention. FIG. 1A shows a lactose monoacetate ester, while FIG. 1B depicts a sophorose diacetate ester. FIG. 1C shows a maltose diacetate ester. All three compounds are esterified at the 6′ and/or 6 position.

Figure 2:
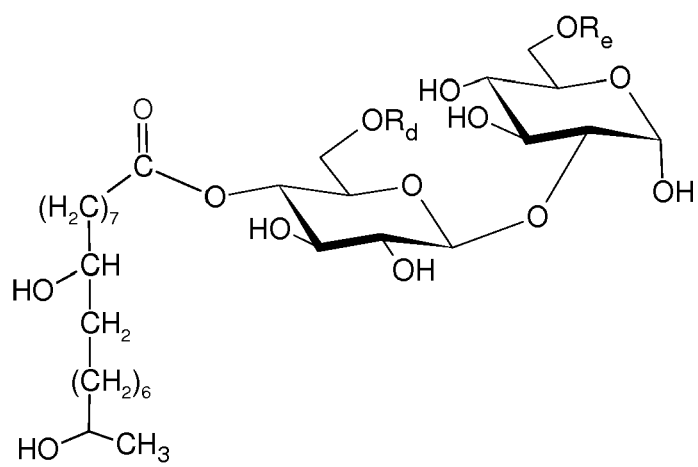
FIG. 2 shows examples of two additional compounds resulting from the formic acid treatment of lactonic sophorolipid containing a monounsaturated fatty acyl moiety: (A) sophorose ester with a 17-hydroxy fatty acyl group substituted with an additional hydroxyl at 9 position and (B) at 10 position. In this figure, $R_d$=H or C(O)CH$_3$; $R_e$=H or C(O)CH$_3$; $R_f$=H or C(O)CH$_3$; and $R_g$=H or C(O)CH$_3$.
Figure 2:
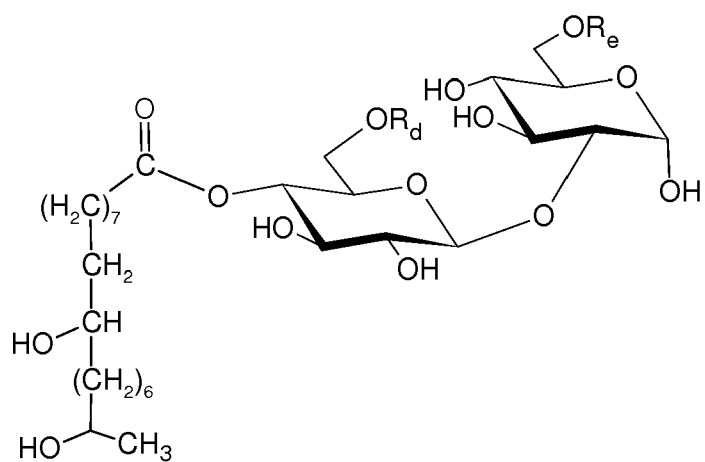
Figure 3:
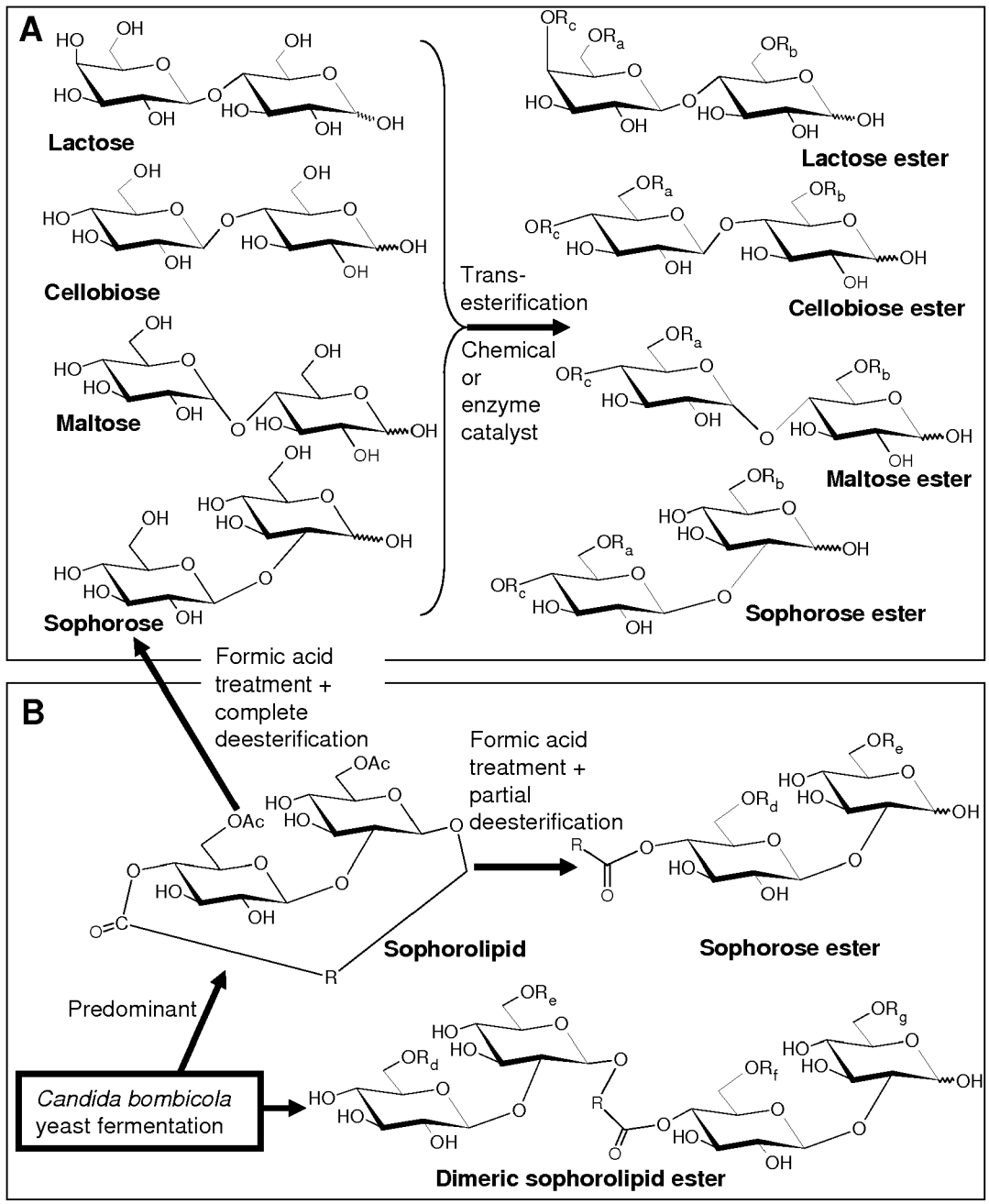
FIG. 3 depicts a synthesis route for the preparation of carbohydrate esters: (A) preparation of lactose, cellobiose, maltose, and sophorose esters through chemical or enzymatically catalyzed trans-esterification; and (B) preparation of sophorolipid and dimeric sophorolipid ester through *C. bombicola* fermentation and preparation of sophorose and sophorose ester through formic acid treatment of sophorolipid followed by full and partial de-esterification, respectively. In this figure, $R_a$=H or C(O)R; $R_b$=H or C(O)R; $R_c$=H or C(O)R; $R_d$=H or C(O)CH$_3$; $R_e$=H or C(O)CH$_3$; $R_f$=H or C(O)CH$_3$; and $R_g$=H or C(O)CH$_3$; and R is an aliphatic moiety.

In another embodiment, sophorose esters are produced by the reaction of formic acid or acetic acid with natural lactonic sophorolipids under non-aqueous conditions resulting in a formyl- or acetyl-protected and C-1′ ring-opened sophorolipid. This is followed by partial or complete cleavage of the formate or acetate esters from the treated sophorolipid. Other side products, such as unmodified sophorolipids and higher esters (esters with DS>3), may also be present. FIG. 1D depicts a deacetylated or 6′ and/or 6″ acetylated alpha-sophorose ester esterified at C-4″ position with an 18-carbon monounsaturated fatty alcohol hydroxylated at the C-17 position of the fatty alcohol chain. The compound was produced by formic acid reaction of natural diacetylated lactonic sophorolipid (obtained from the culture of *C. bombicola*) catalyzed by sulfuric acid followed by cleavage of formate ester from the treated parent compound by heating or refluxing the substrate in an acetic acid and methanol mixture. Sulfuric acid is an inexpensive and readily available catalyst. Formic acid can also participate in an addition reaction with lactonic sophorolipids that contain unsaturation on their fatty acyl moiety and may result in the formation of a hydroxyl group on the unsaturated positions upon the cleavage of formate ester. Two exemplary products are provided in FIG. 2 that result from the formic acid treatment of lactonic sophorolipid containing an 18-carbon fatty acyl moiety monounsaturated at 9 position. FIG. 2A and FIG. 2B depict a sophorolipid ester with a 17-hydroxy fatty acid substituted with an additional hydroxyl at 9-position and 10-position, respectively.

In another aspect, a sophorose dimer is produced by the yeast C. bombicola using the method of the invention. The compound may be isolated from the crude culture of C. bombicola where other side products may consist of natural acetylated lactonic or acidic sophorolipid. FIG. 1E depicts a deacetylated or 6' and/or 6" acetylated sophorolipid dimer ester esterified at C-4" position with an 18-carbon monounsaturated fatty chain. The compound is produced by fermentation of C. bombicola using glucose and canola oil as feedstock.

The lactose, sophorose, cellobiose, maltose, isomaltose esters, sophorose ester (obtained from formic acid treatment of natural lactonic sophorolipid), and the sophorolipid dimer produced by the method of the invention have the structures depicted by formula (I), (II), (III), (IV), (V), (VI), and (VII), respectively:

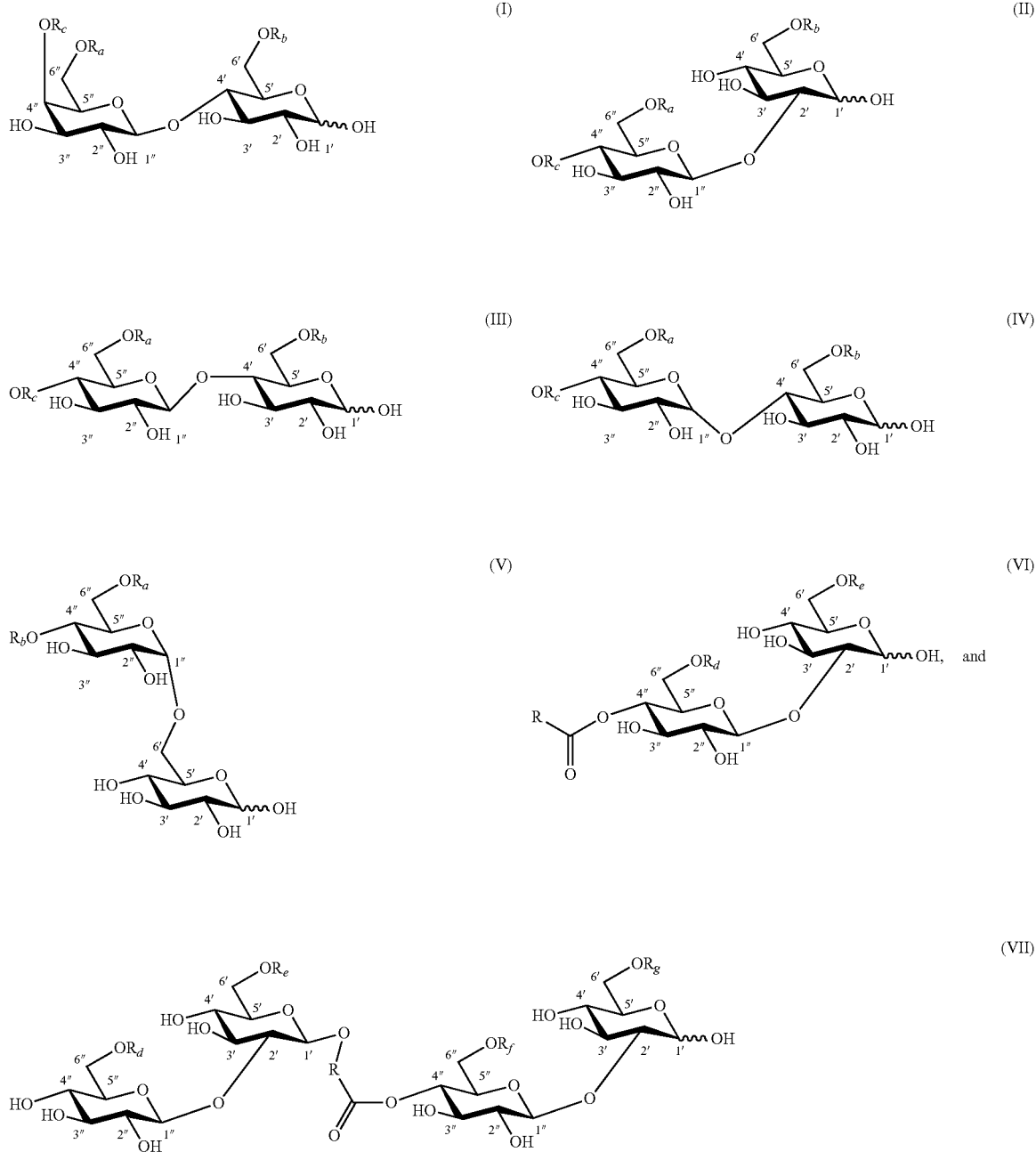

where $R_a$ is H or C(O)R;
$R_b$ is H or C(O)R;
$R_c$ is H or C(O)R;
$R_d$ is H or C(O)CH$_3$;
$R_e$ is H or C(O)CH$_3$;
$R_f$ is H or C(O)CH$_3$;
$R_g$ is H or C(O)CH$_3$; and
R is an aliphatic moiety, with the proviso that in formula (II), $R_c$ is H when $R_a$ is H or C(O)CH$_3$ and $R_b$ is H or C(O)CH$_3$.

In some embodiments, R is an aliphatic moiety selected from unsubstituted C$_1$-C$_{24}$ alkyl, substituted C$_1$-C$_{24}$ alkyl, unsubstituted C$_2$-C$_{24}$ alkenyl, and substituted C$_2$-C$_{24}$ alkenyl.

In other embodiments, R is an aliphatic moiety selected from C$_1$-C$_{24}$ alkyl substituted with hydroxyl groups and C$_2$-C$_{24}$ alkenyl substituted with hydroxyl groups.

In further embodiments, R is an aliphatic moiety selected from C$_1$-C$_{24}$ alkyl substituted with carboxyl groups and C$_2$-C$_{24}$ alkenyl substituted with carboxyl groups.

In certain embodiments, R is an aliphatic moiety selected from C$_1$-C$_{24}$ alkyl substituted with aromatic groups and C$_2$-C$_{24}$ alkenyl substituted with aromatic groups.

In some embodiments, the esters produced by the method of the invention have the structures depicted by compounds of formula (Ia), (IIa), (IIIa), (IVa), (Va), (VIa), or (VIIa):

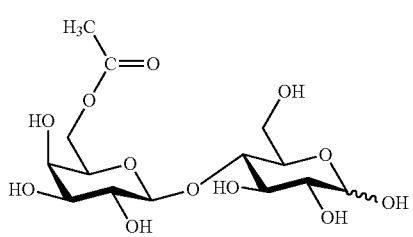
(Ia)

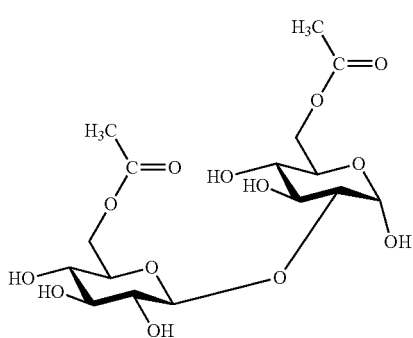
(IIa)

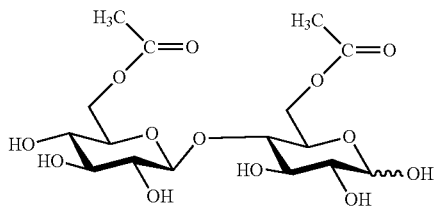
(IIIa)

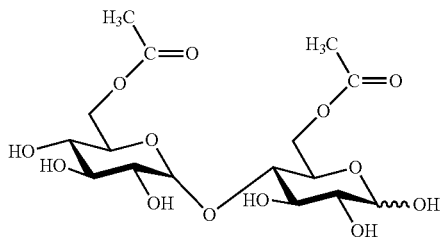
(IVa)

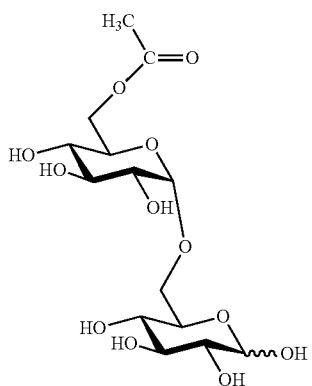
(Va)

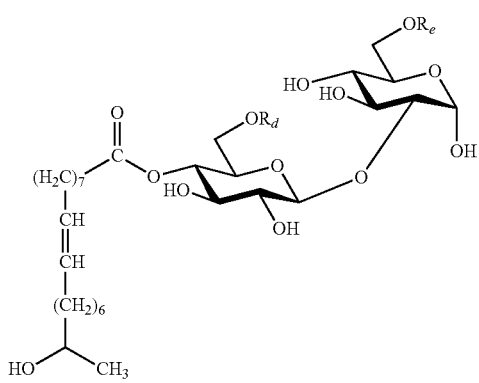
(VIa)

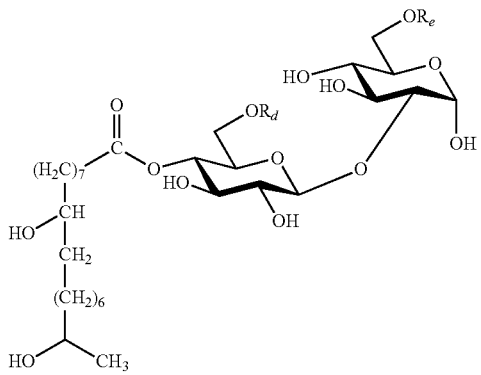
(VIb)

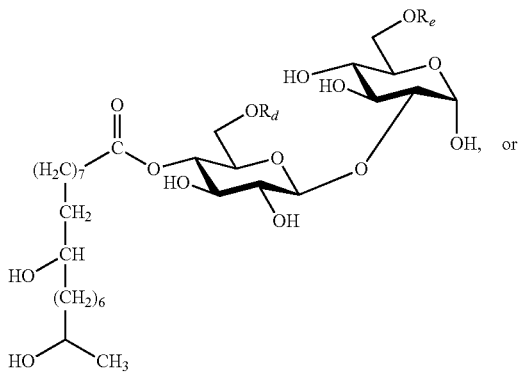
(VIc)

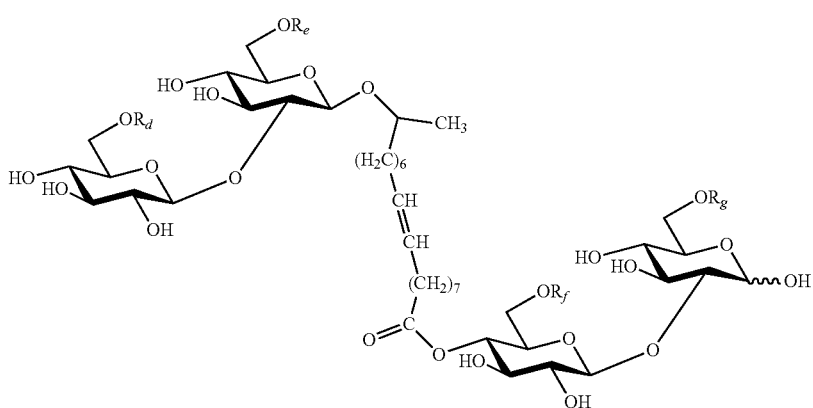
(VIIa)

where $R_d$ is H or $C(O)CH_3$; $R_e$ is H or $C(O)CH_3$; $R_f$ is H or $C(O)CH_3$; and $R_g$ is H or $C(O)CH_3$.

In a further embodiment, the sophorose ester is a novel compound having a structure of formula (II):

(II)

wherein:
$R_a$ is H or $C(O)R$;
$R_b$ is H or $C(O)R$;
$R_c$ is H or $C(O)R$; and
R is an aliphatic moiety, with the proviso that $R_c$ is H when $R_a$ is H or $C(O)CH_3$ and $R_b$ is H or $C(O)CH_3$.

As used herein, an "aliphatic" moiety is a non-aromatic carbon moiety. In some embodiments, an aliphatic moiety may include a linear, branched or cyclic carbon moiety. In certain embodiments, an aliphatic moiety may include a saturated or unsaturated moiety, including both monovalent and bivalent moieties. In some embodiments, the aliphatic moiety is an aliphatic alkyl, an aliphatic alkenyl, an aliphatic alkynyl, an aliphatic cycloalkyl, an aliphatic cycloalkenyl, an aliphatic cycloalkynyl, or any bivalent radicals thereof.

"Alkyl" includes saturated linear or branched hydrocarbon structures, and combinations of these, which contain only carbon and hydrogen atoms when unsubstituted. In some embodiments, alkyl groups have one to twenty-four carbon atoms (i.e., $C_1$-$C_{24}$ alkyl), five to twenty-four carbon atoms (i.e., $C_5$-$C_{24}$ alkyl), or fifteen to eighteen carbon atoms (i.e., $C_{15}$-$C_{18}$ alkyl). When an alkyl residue having a specific number of carbon atoms is named, all geometric isomers having that number of carbon atoms may be encompassed. For example, "butyl" may, in some embodiments, include n-butyl, sec-butyl, iso-butyl, and tert-butyl; "propyl" may, in some embodiments, include n-propyl and iso-propyl. In some embodiments, the alkyl group may be substituted. In one embodiment, substituted alkyl groups may have a hydroxyl substituent. Alkyl groups substituted with hydroxyl may include, for example, —$(CH_2)_2OH$ and —$(CH_2)_4OH$. In another embodiment, substituted alkyl groups may have a carboxyl substituent. Alkyl groups substituted with carboxyl may include, for example, —$(CH_2)_2COOH$. In another embodiment, substituted alkyl groups may have an aromatic substituent. Alkyl groups substituted with aromatic may include, for example, —$CH_2$(phenyl).

"Cycloalkyl" refers to a cyclic alkyl group, and can have one ring (e.g., cyclohexyl) or multiple rings (e.g., adamantyl).

"Alkylene" refers to the same residues as alkyl, but having bivalency. Examples of alkylene include methylene (—$CH_2$—), ethylene (—$CH_2CH_2$—), propylene (—$CH_2CH_2CH_2$—), butylene (—$CH_2CH_2CH_2CH_2$—), as well as longer chains including —$(CH_2)_{17}$—.

"Alkenyl" refers to an unsaturated hydrocarbon group having at least one site of olefinic unsaturation (i.e., having at least one moiety of the formula —C═C—). When the alkenyl has one site of olefinic unsaturation, the alkenyl is monounsaturated. When the alkenyl has two or more sites of olefinic unsaturation, the alkenyl is polyunsaturated. In some embodiments, alkenyl groups have two to twenty-four carbon atoms (i.e., $C_2$-$C_{24}$ alkenyl), five to twenty-four carbon atoms (i.e., $C_5$-$C_{24}$ alkenyl), or fifteen to eighteen carbon atoms (i.e., $C_{15}$-$C_{18}$ alkenyl). Alkenyl groups may include, for example, —$CH_2$—$CH$=$CH$—$CH_3$ and —$(CH_2)_7$—$CH$=$CH$—$(CH_2)_7$—$CH_3$. In some embodiments, the alkenyl group may be substituted. In one embodiment, substituted alkenyl groups may have a hydroxyl substituent. Alkenyl groups substituted with hydroxyl may include, for example, —$(CH_2)_2OH$ and —$(CH_2)_4OH$. In another embodiment, substituted alkenyl groups may have a carboxyl substituent. Alkenyl groups substituted with carboxyl may include, for example, —$(CH_2)_2COOH$. In another embodiment, substituted alkenyl groups may have an aromatic substituent. Alkenyl groups substituted with aromatic may include, for example, —$CH_2$(phenyl).

"Cycloalkenyl" refers to a cyclic alkenyl group and can have one ring (e.g., cyclohexenyl, —$CH_2$—$CH_2$-cyclohexenyl), or multiple rings (e.g., norbornenyl).

"Alkenylene" refers to the same residues as alkenyl, but having bivalency. Examples of alkenylene include ethylene (—$CH$=$CH$—), propylene (—$CH_2$—$CH$=$CH$—), butylene (—$CH_2$—$CH$=$CH$—$CH_2$—), as well as longer chains including —$(CH_2)_7$—$CH$=$CH$—$(CH_2)_8$— and —$(CH_2)_7$—$CH$=$CH$—$(CH_2)_6$—$CH$=$CH$—.

Unless otherwise specified, the carbohydrate esters of the present invention depicted by structures with formula (I) through (VII) and (Ia) through (VIIa) have the following glycosidic linkages: formula (I), (Ia), lactose (gal(beta 1, 4)glc); formula (II), (IIa), sophorose (glc(beta 1, 2)glc); formula (III), (IIIa), cellobiose (glc(beta 1, 4)glc); formula (IV), (IVa), maltose (glc(alpha 1, 4)glc); formula (V), (Va), isomaltose (glc(alpha 1, 6)glc); formula (VI), (VIa), sophorose (glc(beta 1, 2)glc); and formula (VII), (VIIa), sophorose (glc(beta 1, 2)glc).

Uses of the Carbohydrate Esters

One or more carbohydrate esters produced by the methods described herein, or any compositions thereof, can be used as inducers that cause cells to produce large amounts of enzymes or other substances than they would otherwise produce if the inducer were absent. Isolated and purified carbohydrate esters produced by the present methods may be used as inducers or the crude reaction mixture containing the carbohydrate esters may be used as an inducer without further purification.

In one aspect, one or more of the carbohydrate esters produced by methods of the invention described herein, or any compositions thereof, can be used for inducing protein production (e.g., cellulase or amylase production) in fermentation host organisms capable of producing cellulase or amylase in a liquid culture containing an appropriate carbon source. For example, in certain embodiments, one or more carbohydrate esters with a structure of formula (I) through (VII), or any compositions thereof, can be used to induce protein production. Examples of such organisms include filamentous fungi, which have the ability to metabolize cellulose or starch by producing cellulases or amylase that can hydrolyze the beta-(1,4)-linked glycosidic bonds of cellulose or alpha-(1,4)-linked glycosidic bonds of starch to produce glucose.

Suitable filamentous fungi may include all filamentous forms of the subdivision Eumycotina. (See, Alexopoulos, C. J. (1962), *Introductory Mycology*, Wiley, New York). These fungi are usually characterized by a vegetative mycelium with a cell wall composed of chitin, cellulose, and other complex polysaccharides. Suitable species of filamentous fungi or bacteria or other hosts for use with the carbohydrate ester inducers of the present invention include, for example, hosts selected from the following genera: *Trichoderma, Humicola, Pleurotus, Fusarium, Aspergillus, Streptomyces, Thermomonospora, Bacillus, Cellulomonas, Penicillium,* Basidiomycete, Chrysoporium, *Pestalotiopsis, Neurospora, Cephalosporium*, Achlya, Podospora, Endothia, *Mucor, Cochliobolus, Myceliopthora, Talaromyces* and Pyricularia. Specific hosts may include, for example, *Trichoderma reesei* (QM 9414, MCG 77, MCG 80, Rut-C30, CL-847, VTT-D, SVG, and RL-P37) (see Esterbauer et al., *Bioresource Tech.,* 36(1):51-65, (1991)), *Aspergillus niger, Aspergillus oryzae, Bacillus subtilis, Penicillium decumbens, Penicillium funiculosum, Penicillium purpurogenum, Chrysosporium lucknowense, Myceliopthora thermophila,* and *Talaromyces emersonii*.

In some embodiments, one or more of the carbohydrate esters produced by the methods of the present invention, or any compositions thereof, are used to induce protein production (e.g., cellulase or amylase production) in a host cell that is a member of the species of *Trichoderma, Penicillium, Chrysosporium, Humicola, Pleurotus, Fusarium, Aspergillus, Streptomyces,* Thermomonospora, Myceliopthora, *Talaromyces, Bacillus* or Cellulomonas. In certain embodiments, one or more carbohydrate esters, or any compositions thereof, are used to induce protein production (e.g., cellulase or amylase production) in a host cell that is a member of the species of *Trichoderma* or *Aspergillus*. In one embodiment, one or more carbohydrate esters, or any compositions thereof, are used to induce protein production in *Trichoderma reesei, Trichoderma viride, Aspergillus niger,* or *Aspergillus oryzae*. The term "*Trichoderma*" refers to any fungal genus previously or currently classified as *Trichoderma*. In certain embodiments, the carbohydrate ester is one or more esters with a structure of formula ((I) through (VII), or preferably, structures of formula (Ia) through (VIIa).

For industrial enzyme production, conventional inducers such as lactose, cellobiose, cellulose, cellulose hydrolysates, starch hydrolysate, and sophorose from glucose reversion are typically used to induce protein expression in *Trichoderma reesei*, while maltose, maltodextrins, starch, and starch hydrolysates are the inducers of choice for *Aspergillus* spp. In some case, these inducers may not perform optimally due to an insufficient amount or unintended repression by impurities or metabolites. Supplementing conventional inducers with the inducers disclosed herein may increase protein expression over that achievable with conventional inducers alone. Therefore, the use of the inducers of the invention may be useful either alone or in combination with each other or with conventional inducers.

In one embodiment, induction of *Trichoderma* with lactose is augmented by the addition of the sophorose esters with structure shown in FIG. 1D and FIGS. 2A and 2B. In another embodiment, induction of *Trichoderma* with a glucose reversion mixture containing sophorose is augmented by the addition of the sophorose esters with structure shown in FIG. 1D and FIGS. 2A and 2B. In yet another embodiment, induction of *Trichoderma* with a biomass hydrolysate (e.g., cellulose, starch) is augmented by the addition of the sophorose esters with structure shown in FIG. 1D and FIGS. 2A and 2B. In a further embodiment, induction of *Aspergillus* protein expression with maltose or maltodextrins is enhanced by supplementation of the inducer mixture with the maltose ester(s) with structures depicted by formula IV and FIG. 1C.

In another embodiment, sophorose esters with structures of formula II, VI, and VII may be used to induce enhanced protein production in solid phase fermentation. Production of enzymes and other protein products using solid phase fermentation relies on the growth of microbes (in particular, filamentous fungi) on moist solid substrates without free-flowing liquid. In contrast to liquid-submerged fermentation, solid phase fermentation in some situations can offer significant advantages in both performance and production cost. Suitable solid substrates include readily available and inexpensive carbon sources based on agriculture residues such as wheat bran or corn cobs, or mixtures thereof. Suitable filamentous fungi for use in this embodiment have been described above and include *Trichoderma reesei* and *Aspergillus niger*.

The solid substrates are moistened with an appropriate nutrient medium to reach a starting moisture content of 40%, 50%, 60%, or 70% to allow the fungi to grow on the substrate. Prior to use, these solid substrates might be activated by pretreatment with steam and chemicals known to those skilled in the art. Crude or purified sophorose ester is mixed into the solid substrate and fermentation is initiated by inoculating the mixture with an appropriately prepared culture of a suitable filamentous fungi. The resulting product, for example, an enzyme such as cellulase is then isolated from the mixture by methods known in the art. Typical isolation involves washing the solid state fermentation media with a liquid. In some cases, the solid substrate might be pressed and/or a detergent might be added to the washing liquid to improve efficiency. In some applications (e.g., animal feed), the enzymes are not isolated and are used as produced together with the solid substrate.

It should also be understood that the carbohydrate esters described herein, or any compositions thereof, may be used with genetically engineered host cells. To produce proteins with recombinant DNA technology, a DNA construct that includes the nucleic acid encoding the amino acid sequence of the designated protein can be constructed and transferred into, for example, a *T. reesei, Aspergillus niger*, or *Aspergillus oryzae* host cell. The vector may be any vector known in the art which, when introduced into the host cell, can be integrated into the host cell genome and can be replicated. The nucleic acid encoding the protein can be operably linked to a suitable promoter, which shows transcriptional activity in a *Trichoderma* or *Aspergillus* host cell. Suitable promoters may include, for example, cellobiohydrolase 1 (cbh1), endoglucanase, xylanase, glucoamylase A (glaA), and Taka-amylase (amyA). In one exemplary embodiment, the carbohydrate esters described herein with a structure of formula (I), (II), (III), (VI), (VII), or any compositions thereof, may be a powerful inducer of the cbh1 promoter in *Trichoderma*, which may increase cellulase production by several folds compared to other known cellulase inducers. In another exemplary embodiment, the carbohydrate esters described herein with structure of formula (IV), or (V), or any compositions thereof, may be a powerful inducer of the glaA or amyA promoter in *Aspergillus*, which may increase amylase production by several folds compared to other known amylase inducers.

It should be understood, however, that the carbohydrate esters described herein, or any compositions thereof, may induce production of any protein that may be under the control of a native or engineered promoter, such as cbh1 or glaA. The promoter may be derived from genes encoding proteins that may be either homologous or heterologous to the host cell. One of skill in the art would recognize that a promoter can be engineered to enhance its function and the applicability of this new inducer should not be constrained by its alteration. Homologous or heterologous protein expression under this promoter may be routinely carried out using recombinant molecular biology techniques known in the art, which may rely on successful recombination of genes encoding the protein of interest. Examples of homologous and heterologous proteins of interest include, for example, enzymes, hormones, growth factors, cytokines, vaccines, antibodies, and polypeptides. In some embodiments, the carbohydrate esters described herein may induce production of enzymes including, for example, cellulases, amylases, proteases, xylanases, lipases, esterases, phytases, pectinases, catalases, pullulanases, laccases, oxidases, glucose isomerases, lyases, acylases, and transferases.

Fermentation procedures for production of proteins are generally known to one of skill in the art. Generally, cells are cultured in a medium containing physiological salts and nutrients. (See, e.g., Pourquie, J. et al., *Biochemistry and Genetics of Cellulose Degradation*, Aubert, J. P. et al., eds., Academic Press, pp. 71-86, 1988; and Ilmen, M. et al., *Appl. Environ. Microbiol.*, 63:1298-1306 (1997). For example, *Trichoderma* and *Aspergillus* cells may be cultured in the medium as described by England et al. (U.S. Published Patent Application No. 2010/0009408) and by Barton et al. (*J. Bacteriol.*, 111(3):771-777 (1972), respectively. Culture-conditions (e.g., temperature, pH, duration) are also generally known in the art. For example, cultures may be incubated at approximately 28° C. in appropriate medium in shake cultures or fermenters until desired levels of cellulase expression are achieved. After fungal growth has been established, the cells are exposed to conditions effective to cause or permit the expression of the protein. An appropriate carbon source is also provided in the culture medium. Examples of appropriate carbon source biomass include, but are not limited to, glucose, sucrose, fructose, glycerol, lactose, cellulose, cellulose hydrolysate, starch, starch hydroylsate, maltose, or maltodextrin.

One or more of the carbohydrate esters described herein, or any compositions thereof, may be added to the medium at a concentration effective to induce protein production (e.g., cellulase or amylase production). The esters may also be added to the medium in an insoluble or soluble form. In certain embodiments, the carbohydrate esters can be reconstituted in water or one or more solvents (e.g., ethanol, or dimethyl sulfoxide) prior to the introduction into the fermentation culture as a media component or as an inducing feed. Solubilizing the inducers allows for their use as a concentrated feed for protein production in an industrial fed-batch fermentation process. Further, it should be understood that the carbohydrate ester inducers may be used in a batch, fed-batch, or a continuous fermentation process.

The use of one or more of the carbohydrate esters described herein has been found to surprisingly increase cellulase or amylase production by several folds compared to unmodified starting material such as lactose, sophorose, maltose, or natural sophorolipids. In certain embodiments, the use of one or more of carbohydrate esters, or any compositions thereof, can increase cellulase production in a *Trichoderma* host (e.g., *T. reesei*) or amylase production in *Aspergillus* host (e.g., *Aspergillus niger*) by at least three folds, by at least four folds, at least five folds, at least ten-fold, at least twenty-fold, or at least thirty-fold, greater than an unmodified lactose or sophorose. In certain embodiments, the carbohydrate esters are one or more esters with a structure of formula (I) through (VII), or preferably, with a structure of formula (Ia) through (VIIa).

While the carbohydrate esters produced by methods of the present invention may be used to induce protein expression directly as a crude reaction mixture containing other side products, it should also be understood that the active carbohydrate ester components of the crude mixture can be individually separated or isolated, and optionally further purified. For example, in some embodiments, one or more esters with a structure of formula (I) through (VII), or preferably, with a structure of formula (Ia) through (VIIa), may be isolated for use in protein production. In some embodiments, the use of purified lactose monoester or sophorose diester isolated from the crude ester mixture may result in at least a one-fold, at least a two-fold, or at least a three-fold increase in cellulase production in *Trichoderma* compared to the use of an unpurified crude mixture. It should be understood that the unmodified lactose or sophorose is the one from which the lactose and sophorose esters were prepared.

The embodiments in the specification are selected to best explain the principles of the invention and its practical use under the described conditions that might not be optimized. One of skill in the art would recognize the induction power of these novel inducers may be enhanced by variations in process conditions and by the alterations made to the production host. The applicability of this invention should not be constrained by these variations.

Method of Preparing Carbohydrate Esters

Provided herein are methods of producing lactose, sophorose, cellobiose, maltose, and isomaltose esters by enzymatic or chemically catalyzed trans-esterification of unmodified disaccharides with a vinyl ester. Several methods are currently known in the art for esterifying carbohydrates including, for example, chemical or enzymatic synthesis of sucrose esters (Polat and Linhardt, *J. Surfact. Deterg.*, 4(4):415-421 (2001)), enzymatic synthesis of a maltose monolaurate ester (Plou et al., *J. Biotech.*, 96:55-66 (2002)) and a lactose monolaurate ester (U.S. Patent Application Publication No. 2011/0257108), and chemical synthesis of a maltose monostearate (Allen and Tao, *J. Surfact. Deterg.*, 5(3):245-255 (2002)).

One or more compounds of formula (I) through (V) are prepared by: a) providing a disaccharide such as lactose, sophorose, cellobiose, maltose, or isomaltose, preferably dry and preferably in high purity; and b) contacting the disaccharide with a vinyl ester and an enzyme or chemical catalyst in a suitable solvent system to produce the composition. In some embodiments, the reaction mixture is heated to a temperature of 40° C. to 100° C. In other embodiments, the acid hydrolysis may be performed at a temperature of at least 40° C., at least 50° C., at least 60° C., at least 70° C., at least 80° C., at least 90° C., or at least 100° C. In yet another embodiment, the method for producing a composition that includes one or more compounds of formula (I) through (V), further includes vacuum distillation to remove the solvent; and isolating the product of interest from the composition.

Vinyl esters may be fatty acid vinyl esters or aromatic vinyl esters. Suitable fatty acid vinyl esters include vinyl acetate, vinyl propionate, vinyl butyrate, vinyl methacrylate, vinyl oleate, vinyl linoleate, vinyl palmitate, and vinyl stearate. Examples of aromatic vinyl esters include vinyl cinnamate and vinyl caffiate.

Suitable lipase enzymes for use in the method of the present invention include Novozyme 435 (immobilized *Candida antarctica* lipase B), Lipozyme® TL, Lipozyme® RM, and Amano lipase PS.

In some embodiments, the enzyme catalyst can be replaced with a chemical catalyst (e.g., potassium carbonate ($K_2CO_3$), sodium hydroxide (NaOH), sulfuric acid ($H_2SO_4$), and hydrochloric acid (HCl)) and the vinyl ester can be replaced with acyl chlorides (e.g., acetyl chloride or palmitoyl chloride).

Suitable solvents include dimethyl sulfoxide (DMSO), pyridine, dimethylformamide (DMF), methyl ethyl ketone, isobutanol, tert-amyl alcohol, tert-butyl alcohol, tetrahydrofuran, acetone, or mixtures thereof.

In one aspect, the methods described herein involve enzymatically or chemically modifying disaccharides by trans-esterification reaction with a vinyl ester. These modified disaccharide esters are highly inductive to protein production (e.g., cellulase or amylase production) in filamentous fungi host cells (e.g., *Trichoderma* or *Aspergillus*), exceeding the inductive ability of unmodified starting materials by several folds.

The methods described herein typically yield a crude mixture consisting of active carbohydrate ester as component(s). Any separation techniques known in the art may be employed to isolate the active esters, for example, vacuum distillation, precipitation, crystallization, solvent extraction, or column chromatography.

One skilled in the art will recognize many variations can be made following the spirit of the invention. In certain embodiments, other disaccharides and soluble polysaccharides may be modified into potent inducers using the same principles disclosed in this invention. Examples of other disaccharides include sucrose, trehalose, gentiobiose, laminaribiose, and xylobiose. Examples of polysaccharides include cellodextrins and maltodextrins.

Provided herein are also methods for producing novel and highly inductive sophorose esters with a structure of formula of (VI) by formic acid or acetic acid reaction with natural lactonic sophorolipid under substantially non-aqueous conditions followed partial or complete cleavage of formate or acetate esters from the formyl- or acetyl-protected and C-1' lactone ring-opened sophorolipid. In order to obtain a compound with a structure of formula of (VI), a natural lactonic sophorolipid needs to be ring-opened through selective cleavage of the ether-like linkage at the C-1' (the anomeric carbon) position, followed by regeneration of the hydroxyl group of the hydroxy fatty acid, which remains linked by an ester bond to C-4" (as shown in FIG. 1D). Previously described methods for this transformation are limited by the low yields obtained. The inventor disclosed the use of 0.1N hydrochloric acid with natural sophorolipid under aqueous conditions to produce these compounds (International application no.: WO 2013/003291). The present invention comprises a high yield method involving the reaction of formic or acetic acid with natural lactonic sophorolipid carried out under non-aqueous conditions. This new method promotes cleavage of the ether-like linkage (C-1') in preference to the ester linkage (C-4") of the natural lactonic sophorolipid, thus resulting in a high yield. Unintended formate and acetate esters may be formed with the open hydroxyls during the formic acid or acetic acid treatment of sophorolipid, which require cleavage in order to yield compounds described by formula (VI).

The formic acid or acetic acid reactions may be catalyzed by another acid. Examples of suitable acid catalyst include, for example, sulfuric acid ($H_2SO_4$) or hydrochloric acid (HCl), or mixtures of acid catalysts, at a concentration (wt %) between about 0.05% to about 1%. Appropriate concentrations include 0.05%, 0.10%, 0.15%, 0.20%, 0.30%, 0.50%, 0.75%, and 1%. The natural lactonic sophorolipid may be produced by a fermentation host, including, but not limited to, C. bombicola. Substantially non-aqueous conditions may comprise a water content of no more than about 10%, 9%, 8%, 7%, 6%, 5%, 4%, 3%, 2%, 1%, or less than 1%, by weight.

In some embodiments, the acid treatment is performed at elevated temperatures. The formic acid and acetic acid treatment may be characterized as a formolysis and an acetolysis reaction, respectively. In certain embodiments, the formolysis or acetolysis may be performed at a temperature of at least 40° C. In other embodiments, the formolysis or acetolysis may be performed at a temperature of at least 80° C., at least 90° C., at least 100° C., at least 110° C. or at least 120° C. In other embodiments, the formolysis or acetolysis may be performed at a temperature between 40° C. and 120° C., or between 100° C. and 120° C. The natural sophorolipid mixture can be contacted with the acid at elevated temperatures for a range of time, e.g., from minutes to hours.

In one embodiment, the cleavage of formate ester from the lactone ring-opened sophorolipid involves heating or refluxing the starting material in an acetic acid and methanol mixture. For example, the ratio of acetic acid to methanol may be 3:2 (v/v). In another embodiment, the cleavage of acetate esters involves treating the starting material with an acid, for example, HCl, or a base, for example, ammonia, or an enzyme, for example, esterase. The cleavage of the formate or the acetic ester from the treated sophorolipid may be partial. Migration of fatty and acetyl acyl groups may occur during the cleavage. Further, the lactonic sophorolipid containing single or multiple unsaturation on its fatty acid acyl moiety may participate in an addition reaction with formic acid at the unsaturated positions and the cleavage of formate esters may result in the formation of the hydroxyl group on the unsaturated positions in cases where the sophorose ester contains mono or polyunsaturated fatty acid moieties, for example, in compounds of described in FIG. 2. One of skill in the art would recognize that a partial cleavage of formate and acetate ester, acyl migrations, and hydroxylation of unsaturation may result in new compounds that may be equal to or more inductive than the compounds with structures depicted by (VI). The applicability of this method is not be constrained by this variation.

In another embodiment, the natural lactonic sophorolipid may be first pretreated with formic anhydride or acetic anhydride to yield a compound that is protected by formic and/or acetic esters on all open hydroxyls. This is then followed by the formic and acetic acid treatment to selectively cleave the sophorolipid lactone ring at the C-1' anomeric position and followed by the partial or complete cleavage of formic and acetic ester from the hydroxyls. One of skill in the art would recognize this pretreatment may result in a significant increase in yield with an improved selectivity at the C-1' anomeric position.

In yet another embodiment, the natural laconic sophorolipid may be first pretreated with a hydrogenation reaction to remove potential unsaturations on its fatty acyl group (e.g., monounsaturated 17-hydroxy oleic acid, diunsaturated 17-dihydroxy linoleic acid). One of skill in the art would recognize that this pretreatment may result in a significant reduction in side products being produced, with the final product primarily consisting of a sophorose ester with a saturated fatty acyl group. A more convenient work up may also result from the hydrogenation pretreatment.

Provided herein is also a method for using sophorolipid dimer described by formula (VII) as a highly potent inducer. This compound was recently described by Price et al. (Carbohyd. Res., 348:33-41 (2012), although Price et al. did not recognize its potential in gene induction. In contrast to other known natural sophorolipids (e.g. acetylated and deacylated lactonic or acidic sophorolipids), even if the dimeric sophorolipid exists in trace amounts, it is surprisingly inductive to gene expression in Trichoderma, as described herein. Suitable fermentation hosts for the sophorolipid dimer include, for example, C. bombicola. Examples of an appropriate feedstock for this fermentation method comprises glucose and a vegetable oil, including, but not limited to, canola, soybean, corn, or palm oil. In certain embodiments, compounds of formula (VII) may be isolated as a crude mixture from the culture of Candida bombicola, and still possess surprisingly strong inductive effects.

Also provided herein is a method of producing sophorose by reacting formic acid with natural sophorosides under non-aqueous conditions, followed by complete cleavage of unwanted formate esters. Several low yield methods are currently known in the art that include direct synthesis (Coxon and Fletcher, J. Org. Chem., 26(8):2892-2894 (1961)), acetic acid and hydrobromic acid reaction with stevioside octacacetate followed by deacetylation (Vis and Fletcher, J. Am. Chem. Soc., 78:4709-4710 (1956)), and a dilute hydrochloric acid treatment of stevioside followed by purification (Kusakabe et al., Agric. Biol. Chem., 51 (8): 2255-2256 (1987)).

The present invention describes a simple method of using formic acid reacting with natural sophorosides under non-aqueous conditions followed by cleavage of unwanted formate ester that gives an improved yield of sophorose. In one aspect, a sophoroside is any compound that consists of sophorose as one of its component. Examples of sophorosides include stevioside, sophorolipids and flavonoid sophorosides. In one embodiment, the formic acid reactions may be catalyzed by another acid. Examples of suitable acid catalyst include sulfuric acid ($H_2SO_4$) and hydrochloric acid (HCl), or mixtures of acid catalysts, at a concentration (wt %) between about 0.05% to about 1%. Appropriate concentrations include 0.05%, 0.10%, 0.15%, 0.20%, 0.30%, 0.50%, 0.75%, and 1%.

In one embodiment, the sophoroside is a sophorolipid is produced from a fermentation host, including, but not limited to, C. bombicola. The substantially non-aqueous conditions may comprise a water content of no more than about 10%, 9%, 8%, 7%, 6%, 5%, 4%, 3%, 2%, 1%, or less than 1%, by weight.

In some embodiments, the formic acid treatment is performed at elevated temperatures. In certain embodiments, the formic acid acid formolysis may be performed at a temperature of at least 40° C. In other embodiments, the formolysis may be performed at a temperature of at least 80° C., at least 90° C., at least 100° C., at least 110° C. or at least 120° C. In other embodiments, the formolysis may be performed at a temperature between 40° C. and 120° C., or between 100° C. and 120° C. The natural sophorolipid mixture can be contacted with the formic acid at elevated temperatures for a range of time, e.g., from minutes to hours.

In one embodiment, the cleavage of formate esters from the treated sophoroside involves treating the reaction mixture with a base in a solvent. Examples of suitable base include, but are not limited to, sodium methoxide ($CH_3NaO$) and ammonia ($NH_3$). Examples of suitable solvents include, but are not limited to, methanol, ethanol, and 1-propanol.

In another embodiment, the sophorosides may be first pretreated with formic anhydride or acetic anhydride to yield a compound that is protected by formic and/or acetic esters on all open hydroxyls. This pretreatment is then followed by the formic acid treatment to selectively cleave the sophorosides at the C-1' anomeric position, followed by complete cleavage of formic and acetic ester from the hydroxyls. One of skill in the art would recognize this pretreatment may result in a significant increase in yield of sophorose due to an improved selectivity at the C-1' anomeric position.

In yet another embodiment, the formic acid treatment of a sophoroside based on natural lactonic and/or acidic sophorolipid may be carried out first after a hydrogenation reaction to remove potential unsaturations on its fatty acyl group. One of skill in the art would recognize this pretreatment may result in a significant reduction in side products being produced and a more convenient work up for sophorose is expected as a result of the hydrogenation pretreatment of the sophorolipids.

Sophorose may be isolated and purified from the final reaction mixture through methods known in the art. Suitable purification methods include, for example, chromatography, adsorption, extraction, precipitation, re-precipitation, crystallization, and recrystallization.

Method of Preparing Natural Lactonic Sophorolipid and Dimeric Sophorolipid

The afore-mentioned natural lactonic sophorolipid mixture and sophorolipid dimers may be prepared from microbial cultures using yeast. Suitable yeast strains may be selected from, for example, the following genera: *Candida, Starmerella, Rhodotorula*, and Wickerhamiella. Specific strains suitable for sophorolipid production include, for example, *C. bombicola* (e.g., ATCC 22214, NRRL Y-30816), Starmerella *bombicola, Candida apicola, Candida riodocensis, Candida stellata*, and *Candida* sp. NRRL Y-27208. (See Kurtzman et al., *FEMS MicrobioL Lett.,* 311:140-146 (2010)).

In some embodiments, the natural sophorolipid mixture is produced by the yeast *C. bombicola* or *Candida* apicola. For example, *C. bombicola* has an active extracellular lipase system that first cleaves triglycerides from vegetable oil into free fatty acids, which are readily taken up by the yeast. The fatty acids then undergo hydroxylation at the ultimate or penultimate carbon through the action of cytochrome P450. Sophorose is then added onto the hydroxylated fatty acid by the actions of two glycosyltransferases. (See Fleurackers, *Eur. J. Lipid Sci. Technol.,* 108: 5-12, (2006)). Acetylation and lactonization complete the formation of sophorolipids, which are then secreted by the yeast.

Fermentation procedures for production of sophorolipids are generally known to one of skill in the art. Suitable carbon substrates used in the fermentation to produce the natural sophorolipids may include hydrophobic substrates, for example, vegetable oils (e.g., canola, soy, corn, palm, coconut, sunflower seed, cottonseed, or olive oils), fatty acids (e.g., palmitic, oleic, elaidic, linoleic, alpha-linolenic, or stearic acids), fatty acid esters (e.g., fatty acid methyl ester or fatty acid ethyl ester), alkanes (e.g., pentadecane, hexadecane, heptadecane, or octadecane), and fatty alcohols (e.g., pentadecanol, hexadecanol, heptadecanol, or octadecanol).

The length of the carbon substrates used in the fermentation to produce the natural sophorolipids generally depend on the fermentation host. For example, in certain embodiments where a *Candida* host (e.g., *C. bombicola*) is used, the fatty acids and/or alkanes have a chain length of between fifteen and eighteen carbon atoms. In one variation, fatty acids with carbon chains of between fifteen and eighteen carbon atoms may be preferable to alkanes with carbon chains of between fifteen and eighteen carbon atoms. (See Van Bogaert et al., *Process Biochem.,* 46(4): 821-833 (2011)). In one embodiment, the carbon substrate used in the fermentation to produce the natural sophorolipids is canola oil, which has a high $C_{18}$ content and a monounsaturated fatty acid chain. Further, it should also be understood that other longer or shorter carbon substrates can be used, but can be reduced or elongated to between 15 and 18 carbon-member chains for use with a *Candida* host.

Yeast typically produces a mixture of sophorolipids, and the sophorolipid molecules of the mixture usually have one sophorose molecule linked to a hydroxylated fatty acid at the C-1' position of the sophorose molecule. The natural sophorolipid mixture may include diacetylated sophorolipids in either lactonic or acidic forms. For natural sophorolipid mixtures produced by *C. bombicola*, diacetylated lactonic sophorolipids are typically present in a greater amount (e.g., greater than 60%) than acidic sophorolipids (e.g., less than 10%). See Asmer et al., *J. Am. Oil Chem. Soc.,* 65(9):1460-1466 (1988); Davila et al., *J. Chromatography,* 648:139-149 (1993); Davila et al., *J. Indust. Microbio.,* 13: 249-257 (1994); Ratsep & Shah, *J. Microbio. Methods,* 78:54-356 (2009). The sophorolipids of the natural sophorolipid mixture typically have acetyl groups at the C-6" and/or C-6' positions of the sophorose molecule. See Van Bogaert et al., *Process Biochemistry* 46(4):821-833 (2011). The fatty acid groups may be saturated or unsaturated, and may vary in length. Typically, sophorolipids in a natural sophorolipid mixture have a fatty acid chain of sixteen to eighteen carbon atoms.

The composition of the natural sophorolipid mixture may depend on the type of feedstock and culture conditions. For example, if the feedstock is a fatty acid ester rather than vegetable oil or free fatty acids, more of the free acidic sophorolipids may be produced. (See Ashby et al., U.S. Published Patent Application No. 2006/0199244.) On the other hand, if an alkane such as hexadecane or heptadecane is used, more of the lactonic sophorolipids are produced. (See Glenns and Cooper, *J. Am. Oil Chemist Soc.,* 83(2): 137-145 (2006).)

The following examples are intended only to further illustrate the invention and are not intended to limit the scope of the invention as defined by the claims.

EXAMPLES

Example 1. Enzymatically Prepared Lactose Acetate Ester for Inducing Gene Expression in *Trichoderma*

This example describes the preparation of the lactose acetate esters depicted in FIG. 1A from lactose using enzyme-catalyzed trans-esterification, which enhances their protein induction power in *Trichoderma*.

The preparation starts first with dissolving 25 mg of D-lactose (Sigma-Aldrich) with 0.20 mL of dimethyl sulfoxide (DMSO) in a 20 mL glass scintillation vial. This was followed with the addition of 1.8 mL of tert-amyl alcohol, 0.125 g of molecular sieve (SYLOSIV, WR Grace, Columbia, Md.), and 0.125 g of immobilized lipase enzyme (Lipozyme TL, Novozymes, Franklinton, N.C.). The mixture was pre-incubated inside a shaker incubator at 50° C. and 150 RPM for 1 hour after which 0.142 mL vinyl acetate (Sigma-Aldrich, St. Louis, Mo.) was added to initiate the trans-esterification reaction. The reaction was allowed to progress for 16 hours inside the shaker incubator at 50° C. and 150 RPM.

At the end of the reaction, the crude product mixture was removed from the scintillation vial and recovered as the supernatant via centrifugation where the solvents were evaporated using a SpeedVac concentrator (Savant, Thermo Scientific). For NMR and induction studies, the lactose monoacetate was fractionated from the crude mixture by flash chromatography. A 5 g self-packed silica gel (Fisher, 230-400Mesh) column was used with an eluent (1-propanol:ethyl acetate:water, 4:5:1) with isocratic elution.

The purity of the lactose monoacetate ester was confirmed via LC-MS using a Waters 2695 HPLC with Waters ZQ 2000 Mass spectrometer and a Waters 2487 UV detector. The analysis was conducted using a Waters Symmetry C18 column (4.6×250 mm, 5 μm) with a (5%/95%) acetonitrile and water eluent containing 0.1% formic acid as the mobile phase run isocratically for a total run time of 15 minutes.

To prepare for protein induction studies using *Trichoderma*, a citrate minimal media was first prepared. The media composition, as modified from England et al. (U.S. Pat. No. 7,713,725), consists of 14.4 g/L citric acid, 4 g/L $KH_2PO_4$, 6.35 g/L $(NH4)_2SO_4$, 2 g/L $MgSO_4$-$7H_2O$, 0.53 g/L $CaCl_2$-$2H_2O$, and trace metal elements at 1 mL/L comprising 5 g/L $FeSO_4$-$7H_2O$, 1.6 g/L $MnSO_4$—$H_2O$, and 1.4 g/L $ZnSO_4$-$7H_2O$. The final pH was adjusted to 5.50 using NaOH. *T. reesei* Rut-C30, a cellulase hyper-secretor, was selected as the host to test for protein expression. It was obtained from ATCC (56765) and developed as a catabolic de-repressed strain from classic mutagenesis of parent strain NG14 and the wild type QM6A (Seidl et al., *BMC Genomics*, 9:327, (2008)). To propagate *Trichoderma*, the freeze-dried stock from ATCC was first dissolved in sterile deionized water and then transferred onto a PDA (potato dextrose agar) plate (Teknova P0047) using a sterile loop. The PDA plate was maintained at room temperature under white fluorescent light and after approximately 7 days, green *Trichoderma* spores could be seen. In addition, 60% (w/v) glucose stock was prepared and used both as control and as the carbon source for *Trichoderma* growth.

To initiate protein induction studies, 0.5 mL of glucose stock was first placed into 14 mL of citrate minimal media inside a 125 mL baffled flask, followed by the addition of 0.5 mL of prospective inducer. For the glucose (no inducer) control, 0.5 mL of glucose stock was placed into 14.5 mL minimal media to give a final glucose concentration of 2%. To commence the fermentation, an approximately 1 cm by 1 cm square agar plug was removed from the *Trichoderma* spore-containing PDA agar plate using a sterile loop and placed into the protein induction culture media to be tested. The cultures were placed inside a 28° C. incubator with shaking at 175 RPM. At day 3 of fermentation, the samples were collected and analyzed for CMC (carboxymethylcellulose) endo-glucanase activity. Since the *T. reesei* Rut-C30 is a cellulase hyper-producer, the CMC activity directly correlates with the amount of protein being induced. The CMC activity assay follows a procedure modified from Mandels and Reese with a 0.3 mL reaction volume (*J. Bacteriol.*, 73:269-278, (1957)). One CMC unit denotes the activity that liberates 1 μmol of reducing sugars (expressed as glucose equivalents) in one minute under specified conditions of 50° C. and pH 4.8.

The results for CMC activity assays are given in Table 1, which shows the cellulase activity of known inducers versus the enzymatically prepared crude lactose acetate ester mixture and purified lactose monoacetate. The crude lactose monoacetate mixture, containing both lactose monoacetate and lactose diacetate, is already very powerful and highly efficient. At 0.8 g/L, it easily surpasses the induction power of lactose and cellobiose at 1.0 g/L. Its specific induction power (expressed as units U/mg inducer) is 14 times higher than unmodified lactose.

TABLE 1

| Induction media* | Inducer concentration | | Cellulase activity | |
|---|---|---|---|---|
| | mg/15 mL | mM | U/mL at day 3 | U/mg at day 3 |
| glucose control (2%) | 0 | 0 | 0.28 ± 0.17 | NA |
| lactose (1.0 g/L) | 15 | 2.92 | 0.64 | 0.64 |
| cellobiose (1.0 g/L) | 15 | 2.92 | 0.34 | 0.34 |
| sophorose (0.13 g/L) | 2.0 | 0.38 | 3.58 | 26.9 |
| sophorose (1.3 g/L) | 20 | 3.90 | 15.0 | 11.2 |
| Crude lactose acetate mixture (0.80 g/L) | 12 | NA | 7.07 | 8.84 |
| Purified lactose monoacetate (0.09 g/L) | 1.4 | 0.23 | 2.05 | 22.0 |
| Purified lactose monoacetate (0.51 g/L) | 7.6 | 1.32 | 10.1 | 19.9 |
| Purified lactose monoacetate (1.05 g/L) | 15.8 | 2.73 | 14.0 | 13.3 |

*All media contain 2% glucose as carbon source.

Even though the impure crude lactose ester mixture is highly inductive, an equivalent mass of the purified lactose monoacetate is even more powerful. The specific induction activity of lactose monoacetate at 0.09 g/L, 0.51 g/L, and 1.05 g/L, measured at day 3, is approximately 34, 31, and 21 times that of unmodified lactose, respectively. Furthermore, the specific induction power of the lactose monoacetate at 0.09 g/L (22.0 U/mg) nearly approaches that of sophorose (26.9 U/mg), which is currently the gold standard for cellulase induction in *Trichoderma*.

The purified lactose monoacetate was confirmed by LC-MS to contain a molar mass of 384 (402 $[M+NH_4]^+$ and 407 $[M+Na]^+$). The structure of the lactose monoacetate was further confirmed by analysis using nuclear magnetic resonance (NMR; Varian 400 mHz).

Based on the spectra of $^1H$ NMR, $^{13}C$-NMR, and two dimensional $^{13}C$-$^1H$ HSQC NMR, the lactose monoacetate as depicted in FIG. 1A was confirmed to be an α and β anomer mixture of lactose monoacetylated at 6" position. The assignments of protons and carbons for the isolated lactose monoacetate fraction are summarized in Table 2 below.

TABLE 2

| Functional groups | $^{13}C$-NMR δ(ppm) | $^1H$-NMR δ(ppm) |
|---|---|---|
| Lactose | | |
| 1' | α: 92.57 | α: 4.89 |
| | β: 97.21 | β: 4.32 |
| 2' | α: 72.68 | α: 3.17 |
| | β: 75.07 | β: 2.96 |
| 3' | α: 71.83 | α: 3.59 |
| | β: 75.19 | β: 3.30 |
| 4' | α: 81.89 | 3.27 |
| | β: 81.44 | |
| 5' | α: 70.23 | α: 3.70 |
| | β: 75.38 | β: 3.30 |
| 6' | α: 61.05 | 3.63, 3.72 |
| | β: 61.10 | |
| 1" | α: 104.17 | 4.26 |
| | β: 104.09 | |
| 2" | α: 70.86 | 3.34 |
| | β: 70.80 | |

TABLE 2-continued

| Functional groups | $^{13}$C-NMR δ(ppm) | $^{1}$H-NMR δ(ppm) |
|---|---|---|
| 3" | α: 73.38 β: 73.41 | 3.36 |
| 4" | 68.83 | 3.62 |
| 5" | 72.90 | 3.74 |
| 6" | 64.04 | 4.08, 4.18 |
| Acetyl group | | |
| —C=O | 170.91 | |
| CH$_3$ | 21.28 | 2.02 |

Example 2. Enzymatically Prepared Sophorose Acetate Ester for Inducing Gene Expression in *Trichoderma*

This example shows that sophorose acetate esters can be prepared from sophorose through enzyme-catalyzed trans-esterification, which enhances its protein induction power in *Trichoderma*. The preparation of crude sophorose ester mixture, purified sophorose diacetate, and the subsequent induction study followed the procedure described in Example 1 except the amount of vinyl acetate used was 0.026 mL.

The CMC activity results shown in Table 3 compare the protein induction power of the crude sophorose acetate ester mixture and purified sophorose diacetate ester to that of sophorose. The crude mixture even though impure is already highly efficient and powerful and at 0.17 g/L. Its specific induction power at 70.2 U/mg is ~3 times that of unmodified sophorose. The purified sophorose diacetate ester is even more powerful and at 0.12 g/L. Its specific induction power at 193.3 U/mg is ~7 times that of unmodified sophorose.

TABLE 3

| | Inducer concentration | | Cellulase activity | |
|---|---|---|---|---|
| Induction media* | mg/15 mL | mM | U/mL at day 3 | U/mg at day 3 |
| glucose control (2%) | 0 | 0 | 0.28 ± 0.17 | NA |
| sophorose (0.13 g/L) | 2.0 | 0.38 | 3.58 | 26.9 |
| sophorose (1.3 g/L) | 20 | 3.90 | 15.0 | 11.2 |
| Crude sophorose acetate mixture (0.17 g/L) | 2.5 | NA | 11.7 | 70.2 |
| Purified sophorose diacetate (0.12 g/L) | 1.8 | 0.28 | 23.2 | 193.3 |

*All media contain 2% glucose as carbon source.

The crude sophorose acetate mixture was analyzed by LC-MS using the same procedure described in Example 1 and was found to consist of a mixture of sophorose monoacetate with a mass of 384 (402 [M+NH$_4$]$^+$), diacetate with a mass of 426 (444 [M+NH$_4$]$^+$), and unreacted sophorose. From the LC-MS, the purity of purified sophorose diacetate ester was confirmed.

Example 3. Enzymatically Prepared Sophorose Palmitate Ester for Inducing Gene Expression in *Trichoderma*

This example shows that sophorose palmitate belonging to the structure class with formula (II) can be prepared from sophorose through enzyme-catalyzed trans-esterification to further enhance its protein induction power in *Trichoderma*. The preparation of crude sophorose palmitate ester mixture and the subsequent induction study followed the procedure described in Example 1 except that 5 mg of sophorose was used as the substrate and vinyl palmitate (TCI America, Portland, Oreg.) was used instead of vinyl acetate. Further purification of the crude product mixture was not carried out.

The CMC activity results shown in Table 4 compare the protein induction power of the crude sophorose palmitate mixture to that of sophorose. The crude mixture, even though impure, is already highly efficient and powerful at 0.17 g/L. Its specific induction power at 73.8 U/mg is similar to the crude sophorose acetate mixture (Table 3) and is ~3 times that of unmodified sophorose.

TABLE 4

| | Inducer concentration | | Cellulase activity | |
|---|---|---|---|---|
| Induction media* | mg/15 mL | mM | U/mL at day 3 | U/mg at day 3 |
| glucose control (2%) | 0 | 0 | 0.28 ± 0.17 | NA |
| sophorose (0.13 g/L) | 2.0 | 0.38 | 3.58 | 26.9 |
| sophorose (1.3 g/L) | 20 | 3.90 | 15.0 | 11.2 |
| Crude sophorose palmitate mixture (0.17 g/L) | 2.5 | NA | 12.3 | 73.8 |

*All media contain 2% glucose as carbon source.

The crude sophorose monopalmitate mixture was analyzed by LC-MS using the same procedure described in Example 1 except a mobile phase of (70%/30%) acetonitrile and water containing 0.1% formic acid was used and the purification was run isocratically for a total run time of 30 minutes. The sample was found to consist of a mixture of monopalmitates with a molar mass of 580 (603 [M+Na]$^+$) and dipalmitates with a mass of 818 (841 [M+Na]$^+$).

Example 4. Chemically Prepared Lactose Acetate Ester for Inducing Gene Expression in *Trichoderma*

This example shows that lactose acetate ester can be also prepared from lactose through chemically-catalyzed trans-esterification to enhance its protein induction power in *Trichoderma*.

The procedure starts first with preparing a 0.4 M lactose solution in dimethyl sulfoxide (DMSO). The solution (2 mL) was mixed with 3 mg of potassium carbonate (K$_2$CO$_3$) catalyst and preheated at 50° C. for 30 minutes to activate the catalyst. After removing undissolved catalyst, the reaction was initiated by adding vinyl acetate with differing molar ratios (vinyl acetate: lactose) in order to control the degree of substitution. Each reaction had a volume of 200 μL and was heated to 60° C. for 30 minutes using a thermocycler without stirring. The subsequent sample recovery and induction study followed the procedure described in Example 1.

The results for CMC activity assays are given in Table 5. The crude lactose acetate ester mixture prepared at a vinyl acetate to lactose ratio of 2:1 gave highest induction. It is very powerful and highly efficient compared to cellobiose and lactose. At 0.91 g/L, it easily surpasses the induction power of lactose and cellobiose at 1.0 g/L. Its specific induction power (expressed as units U/mg inducer) is 13 times higher than unmodified lactose and similar to the enzymatically prepared crude lactose acetate mixture (Table 1).

TABLE 5

| Induction media* | Inducer concentration | | Cellulase activity | |
|---|---|---|---|---|
| | mg/15 mL | mM | U/mL at day 3 | U/mg at day 3 |
| glucose control (2%) | 0 | 0 | 0.28 ± 0.17 | NA |
| lactose (1.0 g/L) | 15 | 2.92 | 0.64 | 0.64 |
| cellobiose (1.0 g/L) | 15 | 2.92 | 0.34 | 0.34 |
| sophorose (0.13 g/L) | 2.0 | 0.38 | 3.58 | 26.9 |
| sophorose (1.3 g/L) | 20 | 3.90 | 15.0 | 11.2 |
| Crude lactose acetate mixture (0.91 g/L) (Vinyl acetate:Lactose 4:1) | 13.6 | NA | 5.66 | 6.24 |
| Crude lactose acetate mixture (0.91 g/L) (Vinyl acetate:Lactose 2:1) | 13.6 | NA | 7.37 | 8.13 |
| Crude lactose acetate mixture (0.91 g/L) (Vinyl acetate:Lactose 1:1) | 13.6 | NA | 6.58 | 7.26 |
| Crude lactose acetate mixture (0.91 g/L) (Vinyl acetate:Lactose 1:2) | 13.6 | NA | 6.21 | 6.85 |
| Crude lactose acetate mixture (0.91 g/L) (Vinyl acetate:Lactose 1:4) | 13.6 | NA | 3.89 | 4.29 |

*All media contain 2% glucose as carbon source.

Based on LC-MS analysis, the crude lactose acetate mixture, prepared chemically with a varying vinyl acetate to lactose ratio, consists of a mixture of acetates with multiple degree of substitution. At high vinyl acetate to lactose ratio (e.g. 4:1), majority are triacetates and diacetates while at lower ratio (e.g. 1:4), majority are monoacetates and unmodified lactose. A ratio of 2:1 gave the highest induction, yielding a product consisting of mainly mono, di, and triacetate esters.

Example 5. Chemically Prepared Sophorose Acetate Ester for Inducing Gene Expression in *Trichoderma*

This example shows that sophorose acetate esters can be also prepared from sophorose through chemically-catalyzed trans-esterification and how they can be further purified to enhance their protein induction power in *Trichoderma*. The procedure of preparing sophorose acetate esters chemically follows the same procedure described in Example 4 and subsequent sample recovery and induction study followed the procedure detailed in Example 1 except the crude mixture was further purified based on procedure described in Example 1 to isolate the sophorose diacetate ester.

The results for CMC activity assays are shown in Table 6. The crude sophorose acetate ester mixture, prepared at a vinyl acetate to sophorose ratio of 1:1, gave highest induction. It is very powerful and highly efficient and greatly exceeds the unmodified sophorose. At 0.09 g/L, its specific induction power (expressed as units U/mg inducer) is 5 times higher than unmodified sophorose and the crude mixture is further purified to isolated sophorose diacetate ester and its specific induction is ~8 times higher than unmodified sophorose.

TABLE 6

| Induction media* | Inducer concentration | | Cellulase activity | |
|---|---|---|---|---|
| | mg/15 mL | mM | U/mL at day 3 | U/mg at day 3 |
| glucose control (2%) | 0 | 0 | 0.28 ± 0.17 | NA |
| sophorose (0.13 g/L) | 2.0 | 0.38 | 3.58 | 26.9 |
| sophorose (1.3 g/L) | 20 | 3.90 | 15.0 | 11.2 |
| Crude sophorose acetate mixture (0.13 g/L) (Vinyl acetate:Sophorose 4:1) | 2 | NA | 15.4 | 115.5 |
| Crude sophorose acetate mixture (0.13 g/L) (Vinyl acetate:Sophorose 2:1) | 2 | NA | 17.7 | 132.8 |
| Crude sophorose acetate mixture (0.13 g/L) (Vinyl acetate:Sophorose 1:1) | 2 | NA | 18.1 | 135.8 |
| Crude sophorose acetate mixture (0.09 g/L) (Vinyl acetate:Sophorose 1:1) | 1.37 | NA | 13.4 | 147.0 |
| Crude sophorose acetate mixture (0.09 g/L) (Vinyl acetate:Sophorose 1:2) | 1.37 | NA | 9.45 | 103.5 |
| Crude sophorose acetate mixture (0.09 g/L) (Vinyl acetate:Sophorose 1:4) | 1.37 | NA | 7.68 | 84.1 |
| Purified sophorose diacetate (0.03 g/L) | 0.45 | 0.07 | 6.33 | 211.0 |

*All media contain 2% glucose as carbon source.

Based on LC-MS analysis, the crude sophorose acetate mixture, prepared chemically with a varying vinyl acetate to sophorose ratio, consists of a mixture of acetates with multiple degree of substitution. At high vinyl acetate to sophorose ratio (e.g. 4:1), the products are mainly tri-, tetra-, penta-, and hexa-acetates, while at lower ratio (e.g. 1:4), the products are mainly are di- and mono-acetates and unmodified sophorose. The ratio of 1:1 gave the highest induction, and the majority of the products are mono-, di-, and tri-acetate esters.

The purified sophorose diacetate ester was confirmed by LC-MS to contain a molar mass of 426 (444 [M+NH4]+ and 449 [M+Na]+). The structure of the sophorose diacetate was further confirmed by analysis using nuclear magnetic resonance (NMR; Varian 400 mHz).

Based on the spectra of $^1$H NMR, $^{13}$C-NMR, and two dimensional $^{13}$C-$^1$H HSQC NMR, the sophorose diacetate as depicted by FIG. 1B was confirmed to be an alpha-sophorose diester acetylated at both 6' and 6" position. The assignments of protons and carbons for the isolated sophorose acetate fraction are summarized in Table 7 below.

TABLE 7

| Functional groups | $^{13}$C-NMR δ(ppm) | $^1$H-NMR δ(ppm) |
|---|---|---|
| Sophorose | | |
| 1' | 91.6 | 5.06 |
| 1" | 105.1 | 4.32 |
| 2' | 82.1 | 3.19 |
| 2" | 73.7 | 3.06 |
| 3' | 71.3 | 3.64 |
| 3" | 76.0 | 3.14 |
| 4' | 70.0 | 3.16 |
| 4" | 70.1 | 3.11 |
| 5' | 68.9 | 3.77 |
| 5" | 73.4 | 3.36 |
| 6' a, 6" a | 63.6, 63.9 | 4.02 |
| 6' b, 6" b | | 4.23 |

TABLE 7-continued

| Functional groups | $^{13}$C-NMR δ(ppm) | $^{1}$H-NMR δ(ppm) |
|---|---|---|
| Acetyl group | | |
| —C═O | 170.3 | |
| CH$_3$ (6') | 20.7 | 2.00 |
| CH$_3$ (6'') | 20.7 | 2.01 |

Example 6. Chemically Prepared Maltose Acetate Ester for Inducing Gene Expression in *Aspergillus*

This example shows that maltose acetate ester can be also prepared from maltose through chemically-catalyzed transesterification to enhance its protein induction power in *Aspergillus*. The procedure of preparing maltose acetate chemically and subsequent sample recovery follows the same procedure described in Example 4. To prepare for protein induction studies using *Aspergillus*, a minimum media was first prepared with 1 g/L KH$_2$PO$_4$, 2 g/L NH$_4$Cl, 0.5 g/L MgSO$_4$-7H$_2$O, 0.2 mg/L CuSO$_4$-5H$_2$O, 12.5 mg/L FeSO$_4$-7H$_2$O, 1 mg/L ZnSO$_4$-7H$_2$O, and 0.09 mg/L MnSO$_4$. *Aspergillus niger* (NRRL 330), obtained from ARS culture collection, was maintained on a PDA plate and allowed to sporulate for a week at room temperature. For inoculation, a 2 cm by 2 cm area agar plug was first removed and suspended in 5 mL sterile water. The spores were washed off from agar with vigorous agitation and 1 mL of the suspension was used as inoculum with 14 mL media and 1% sorbitol as carbon source in a 125 mL baffled flask. The cultures were allowed to progress inside a shaker incubator (28° C. and 200 RPM) for 2 days at which time the inducer was added. After additional 24 hours, the cultures were assayed for amylase activity following similar procedures to those detailed by Barton et al. (*J. Bacteriol.*, 1972, 111 (3):771-777).

The results for amylase activity assays are shown in Table 8. The crude maltose acetate ester mixture prepared at a vinyl acetate to maltose ratio of 2:1 gave highest induction. It is more powerful and highly efficient compared to maltose. At 0.05 g/L, its specific induction power (138.1 U/mg) is 3 times higher than unmodified maltose (44.0 U/mg).

TABLE 8

| Induction media* | Inducer concentration | | Amylase activity | |
|---|---|---|---|---|
| | mg/15 mL | mM | U/mL at day 3 | U/mg at day 3 |
| Maltose control (0.05 g/L) | 0.72 | 0.14 | 2.11 | 44.0 |
| Crude maltose acetate mixture (0.05 g/L) (Vinyl acetate:maltose 4:1) | 0.72 | NA | 3.64 | 75.8 |
| Crude maltose acetate mixture (0.05 g/L) (Vinyl acetate:maltose 2:1) | 0.72 | NA | 6.63 | 138.1 |
| Crude maltose acetate mixture (0.05 g/L) (Vinyl acetate:maltose 1:1) | 0.72 | NA | 6.03 | 125.6 |
| Crude maltose acetate mixture (0.05 g/L) (Vinyl acetate:maltose 1:2) | 0.72 | NA | 5.66 | 117.9 |

*All media contain 1% sorbitol as carbon source.

Based on LC-MS analysis, the crude maltose acetate mixture, prepared chemically with a varying vinyl acetate to maltose ratio, consists of a mixture of acetates with multiple degree of substitutions. At high vinyl acetate to maltose ratio (e.g. 4:1), the product is mainly tri-, tetra-, penta-, and hexa-acetates, while at a lower ratio (e.g. 1:2), the product is mainly tri-, di-, and mono-acetates and unmodified maltose. The ratio of 2:1 gave the highest induction, and the product is mainly mono-, di-, and tri-acetate esters.

Example 7. Sophorose Esters Obtained from Formic Acid Treatment of Natural Lactonic Sophorolipid for Inducing Gene Expression in *Trichoderma*

This example describes a highly effective method of using formic acid to convert non-inductive natural lactonic sophorolipid into novel and highly inductive sophorose esters with structures described by FIG. 1D and FIG. 2. To prepare natural lactonic sophorolipid, *C. bombicola* (ATCC 22214) was used. A sample of freeze-dried stock in a glass vial was obtained from ATCC and was first transferred into a yeast extract, peptone, dextrose (YPD) culture broth, then allowed to grow for 48 hours at 28° C. for two days. The culture was then mixed with sterilized glycerol to prepare a final culture containing 20% glycerol. A cell bank was then established using cryovials with 1 mL of seed culture each, and stored at −80° C.

For the production of natural sophorolipids from canola oil, a production medium was first prepared and included the following components: 100 g/L glucose, 10 g/L yeast extract, 1 g/L urea, and 100 g/L canola oil (Crisco, The J.M. Smucker Company, Orrville, Ohio). Based on the data provided from the manufacturer, the canola oil has 64% monounsaturated fat from mainly oleic fatty acid, and 29% polyunsaturated fat from mainly linoleic and alpha-linolenic fatty acids. To initiate the fermentation, a 1 mL seed of *C. bombicola* from a cryovial as prepared above was placed into 50 mL of production medium inside a 250 mL baffled flask incubated at 28° C. and 250 revolutions per minute (RPM). After seven days, sophorolipids appeared in the media as a viscous brown oily phase, and in some cases, the sophorolipid crystallized into a yellow to white colored residue. The brown oily sophorolipid was isolated using a separation funnel and further purified to recover diacetylated lactonic sophorolipids using a self-packed silica gel column (Fisher, 230-400 Mesh) eluted isocractically using ethyl acetate. To recover crystalline sophorolipids consisting of mostly diacetylated lactonic sophorolipid, sophorolipids were allowed to stand until sediment formed, which was recovered by decanting and washing with water followed by freeze drying. The purity of harvested samples was confirmed by the result from LC-MS and found be a diacetylated lactonic sophorolipid derivatized with hydroxy oleate fatty groups with a molar mass of 688 (706 [M+H$_2$NH$_4$]$^+$ and 711 [M+Na]$^+$).

The next step was treatment with formic acid. The process began by dissolving 5 mg diacetylated lactonic sophorolipid in 200 μL formic acid. In certain runs, this step was followed by addition of 0.31 μL (0.15%) of concentrated sulfuric acid. The reaction mixture was heated to 80° C. in a thermocycler for 30 minutes without stirring. Water (1 mL) was then added to precipitate the sample, followed by centrifugation to recover the precipitate and drying in a SpeedVac to remove residual water and formic acid. The dried sample was then solublized in 200 μL acetic acid to methanol (3:2 v/v) solution and heated to 90° C. for 6 hours to cleave unwanted formate ester from the treated sophorolipid. This step was followed with another drying step using a SpeedVac to remove acetic acid and methanol. The final samples, which were a crude mixture of products, were tested for induction in *Trichoderma* following the procedure described in Example 1.

The CMC activity results shown in Table 9 compare the protein induction power of the crude sophorose ester obtained from the formic acid treatment of natural lactonic sophorolipid to other known inducers. The tested samples, even though impure, were highly efficient and powerful compared to known inducers. The natural diacetylated lactonic sophorolipid is not inductive relative to the glucose control and, after formic acid treatment, its specific induction at 0.33 g/L is enhanced 52-fold. If 0.15% sulfuric acid is used together with formic acid, the specific induction is enhanced by as much as 487-fold at a concentration of 0.03 g/L. Even as an impure, crude sample, the specific induction power of the mixture at 496.5 U/mg is 18 times that of sophorose, the current best in class inducer.

TABLE 9

| Induction media* | Inducer concentration | | Cellulase activity | |
|---|---|---|---|---|
| | mg/15 mL | mM | U/mL at day 3 | U/mg at day 3 |
| glucose control (2%) | 0 | 0 | 0.28 ± 0.17 | NA |
| lactose (1.0 g/L) | 15 | 2.92 | 0.64 | 0.64 |
| cellobiose (1.0 g/L) | 15 | 2.92 | 0.34 | 0.34 |
| sophorose (0.13 g/L) | 2.0 | 0.38 | 3.58 | 26.9 |
| sophorose (1.3 g/L) | 20 | 3.90 | 15.0 | 11.2 |
| Untreated diacetylated lactonic sophorolipid (0.33 g/L) | 5 | 0.48 | 0.34 | 1.02 |
| Formic acid treatment (0.33 g/L) | 5 | NA | 17.7 | 53.1 |
| Formic acid + 0.15% sulfuric acid treatment (0.33 g/L) | 5 | NA | 29.5 | 88.5 |
| Formic acid + 0.15% sulfuric acid treatment (0.17 g/L) | 2.5 | NA | 29.3 | 175.8 |
| Formic acid + 0.15% sulfuric acid treatment (0.07 g/L) | 1 | NA | 22.7 | 340.5 |
| Formic acid + 0.15% sulfuric acid treatment (0.03 g/L) | 0.5 | NA | 16.6 | 496.5 |

*All media contain 2% glucose as carbon source.

Example 8. Natural Sophorolipid Dimer Esters Obtained from *C. bombicola* Culture for Inducing Gene Expression in *Trichoderma*

This example illustrates that the natural sophorolipid dimer depicted in FIG. 1E, can also serve as a highly efficient inducer for gene expression in *Trichoderma*. A crude sample containing the sophorolipid dimer was prepared from the cultures of *C. bombicola* according the procedures described in Example 7 and was typically harvested as a brown oily residue. In addition to canola oil, soybean and corn oil were also used as feedstock (Crisco, The J.M. Smucker Company, Orrville, Ohio). In most cases, the *C. bombicola* yeast did not produce the dimeric sophorolipid. In a few cases, a trace amount was produced and its presence was revealed by LC-MS, which showed molar masses of 1030, 1028, 1072, 1070, 1114, and 1112 (1053 [M+Na]$^+$, 1051[M+Na]$^+$, 1095[M+Na]$^+$, 1093[M+Na]$^+$, 1137[M+Na]$^+$, and 1135[M+Na]$^+$, respectively). The molar masses 1030 and 1028 denote a diacetylated sophorolipid dimer derivatized with an oleate or a linoleate fatty group, respectively. The molar masses 1072 and 1070 denote a triacetylated dimer derivatized with an oleate or a linoleate fatty group, respectively. The molar masses of 1114 and 1112 denote a tetra-acetylated dimer derivatized with an oleate or a linoleate fatty group, respectively. These dimeric compounds were not further isolated, and induction studies were carried out using crude samples following the procedures described in Example 1.

The CMC activity results shown in Table 10 compare the protein induction power of the crude sophorolipid dimer mixture obtained from *C. bombicola* culture to other known inducers. The crude samples, even though impure as shown by LC-MS and TLC, are highly efficient and powerful comparing to known inducers. The crude sample that does not contain dimers is significantly less inductive than samples containing dimers. At 0.90 g/L, the specific induction (19.7 U/mg) of the sample containing dimer grown on canola oil is 7 times the induction produced by the sample without dimer and nearly approaches that of sophorose (26.9 U/mg). Since these dimers exist as only trace amounts in the crude sample, purified dimeric compounds once isolated may be even more powerful.

TABLE 10

| Induction media* | Inducer concentration | | Cellulase activity | |
|---|---|---|---|---|
| | mg/15 mL | mM | U/mL at day 3 | U/mg at day 3 |
| glucose control (2%) | 0 | 0 | 0.28 ± 0.17 | NA |
| lactose (1.0 g/L) | 15 | 2.92 | 0.64 | 0.64 |
| cellobiose (1.0 g/L) | 15 | 2.92 | 0.34 | 0.34 |
| sophorose (0.13 g/L) | 2.0 | 0.38 | 3.58 | 26.9 |
| sophorose (1.3 g/L) | 20 | 3.90 | 15.0 | 11.2 |
| Crude sample without dimers grown on canola oil (1.07 g/L) | 16 | NA | 2.90 | 2.72 |
| Crude sample containing dimers grown on canola oil (0.90 g/L) | 12.5 | NA | 16.4 | 19.7 |
| Crude sample containing dimers grown on soybean oil (0.90 g/L) | 12.5 | NA | 14.5 | 17.4 |
| Crude sample containing dimers grown on corn oil (0.90 g/L) | 12.5 | NA | 15.5 | 18.6 |

*All media contain 2% glucose as carbon source.

Example 9. Sophorose Production from Natural Sophorosides Using Formic Acid

In order to be most useful in commercial applications, sophorose needs to become cheaper and more readily available. This example provides a simple and effective method to produce sophorose in high yield from formic acid treatment of natural sophoroside (stevioside and sophorolipid) under non-aqueous conditions. The procedure is similar to that described in Example 7, except that the samples were freeze dried after formic acid treatment and then solublized in 0.5 M sodium methoxide in methanol for 15 minutes at room temperature. This process removes unwanted formate or fatty esters to produce sophorose. After another drying step using a SpeedVac to remove methanol, the sample was analyzed by HPLC (Waters 2695, 401 RI detector, and BioRad HPX-87H column) to determine the sophorose concentration. As a comparison, stevioside was treated with 0.1 N hydrochloric acid to yield sophorose following the procedure detailed by Kusakabe et al. (*Agric. Biol. Chem.*, 1987, 51 (8):2255-2256).

The results in Table 11 show that when compared with the dilute hydrochloric acid treatment described by Kusakabe, the formic acid treatment produces a significantly increased yield. Using stevioside as a starting material, the yield of sophorose tripled using the formic acid treatment. Using diacetylated lactonic sophorolipid as a starting material, the yield of sophorose was doubled when the formic acid treatment was supplemented with addition of 0.15% sulfuric acid.

TABLE 11

| Sophoroside | Treatment | Theoretical sophorose | Recoverable sophorose | Yield |
|---|---|---|---|---|
| 5 mg stevioside | 0.1N HCl, 100° C., 2 hr | 1.91 mg | 0.353 mg | 18.5% |
| 5 mg stevioside | Formic acid, 80° C., 30 min | 1.91 mg | 1.08 mg | 56.5% |
| 5 mg stevioside | Formic acid + 0.15% sulfuric acid, 80° C., 30 min | 1.91 mg | 1.07 mg | 56.0% |
| 5 mg diacetylated lactonic sophorolipid | Formic acid, 80° C., 30 min | 2.4 mg | 0.449 mg | 20.0% |
| 5 mg diacetylated lactonic sophorolipid | Formic acid + 0.15% sulfuric acid, 80° C., 30 min | 2.4 mg | 0.861 mg | 38.4% |

Example 10. Use of Sophorose Ester as Inducer for Gene Expression in Solid Phase Fermentation Production of enzymes and other protein products using solid phase fermentation relies on the growth of microbes (in particular, filamentous fungi) on moist solid substrates without free-flowing liquid. In contrast to liquid-submerged fermentation, solid phase fermentation in some situations can offer significant advantages in both performance and production cost. This example demonstrates that sophorose ester with structures described by FIG. 1D and FIG. 2 can be used as a very effective inducer for cellulase production in solid phase fermentation using $T.$ $reesei$.

The solid substrate used was a 1:1 blend of wheat bran and corn cob purchased from local pet supply store. Each run consisted of 8 grams of this blend placed into a 125 mL flask, which was then sterilized by autoclaving. The citrate minimum media (pH 4.8) described in Example 1 was then added. The amounts of citrate media added were 5.3 mL, 8 mL, 12 mL, 18.7 mL, which gave a starting moisture content of 40%, 50%, 60%, and 70%, respectively. The sophorose ester used was a crude mixture obtained from the formic acid treatment of the natural lactonic sophorolipid (Example 7). For each run, crude sophorose ester (10 mg) premixed with citrate minimum media was then mixed into the solid substrate. Fermentation was initiated by mixing a 2 mL inoculum of $T.$ $reesei$ preculture (from day 2, Example 1) into the solid substrate followed by incubating the flasks at 28° C. without shaking. The solid sample from each flask was harvested at day 3 and washed with ten volumes of 50 mM citrate buffer (pH 4.8) and analyzed for CMC activity as described in Example 1.

The results in Table 12 show that regardless of the starting moisture content, the addition of sophorose ester inducer to the solid substrate was able to significantly improve the cellulase production in the solid phase fermentation using $T.$ $reesei$. At 40%, 50%, 60%, and 70% starting moisture, the observed improvements in cellulase activity per gram solid substrate are 4 fold, 7 fold, 12 fold, and 5 fold, respectively.

TABLE 12

| Induction media (wheat bran:corn cob, 1:1) | Cellulase activity at day 3 (U/g solids) |
|---|---|
| 40% moisture control | 7.40 |
| 40% moisture + 10 mg sophorose ester | 27.6 |
| 50% moisture control | 3.37 |
| 50% moisture + 10 mg sophorose ester | 22.2 |
| 60% moisture control | 1.78 |
| 60% moisture + 10 mg sophorose ester | 21.6 |
| 70% moisture control | 5.45 |
| 70% moisture + 10 mg sophorose ester | 24.6 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for producing a protein of interest, comprising:
   a) providing a fermentation host; and
   b) culturing the fermentation host with a carbon source and an inducer compound of the following formula:

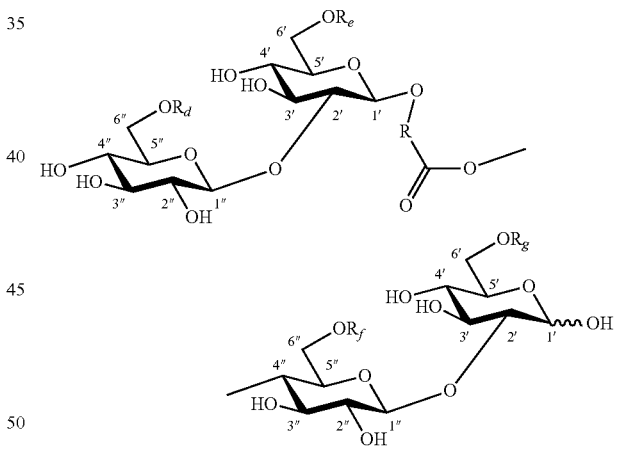

where $R_a$ is H or $C(O)CH_3$; $R_b$ is H or $C(O)CH_3$; $R_c$ is H or $C(O)CH_3$; $R_d$ is H or $C(O)CH_3$; $R_e$ is H or $C(O)CH_3$; $R_f$ is H or $C(O)CH_3$; and $R_g$ is H or $C(O)CH_3$, R is a $C_1$-$C_{24}$ aliphatic moiety, and
   wherein the fermentation host is cultured under conditions sufficient to produce the protein of interest.

2. The method of claim 1, wherein the carbon source comprises one or more of glucose, sucrose, fructose, lactose, cellulose, cellulose hydrolysate, starch, starch hydrolysate, maltose, or maltodextrin.

3. The method of claim 1, wherein the protein of interest comprises a cellulase or an amylase.

4. The method of claim 1, wherein the fermentation host comprises a filamentous fungus of the genus $Trichoderma$ or $Aspergillus$.

5. The method of claim 4, wherein the fermentation host is *Trichoderma reesei, Trichoderma viride, Aspergillus niger,* or *Aspergillus oryzae*.

6. The method of claim 1, wherein the inducer compound is provided in at least trace amounts in an inducer crude mixture.

7. The method of claim 6, wherein the inducer crude mixture is added to the culture in an amount of about 0.9 grams of inducer crude mixture per liter of culture.

8. The method of claim 6, wherein the inducer crude mixture provides a specific induction of greater than or equal to about 17.4 U/mg at day 3.

9. The method of claim 1, wherein R is selected from the group consisting of unsubstituted $C_1$-$C_{24}$ alkyl; $C_1$-$C_{24}$ alkyl substituted with hydroxyl, carboxyl or aromatic groups; unsubstituted $C_1$-$C_{24}$ alkenyl; and $C_1$-$C_{24}$ alkenyl substituted with hydroxyl, carboxyl or aromatic groups.

10. The method of claim 1, wherein R is an aliphatic moiety selected from unsubstituted $C_1$-$C_{24}$ alkyl, substituted $C_1$-$C_{24}$ alkyl, unsubstituted $C_1$-$C_{24}$ alkenyl, and substituted $C_1$-$C_{24}$ alkenyl.

11. The method of claim 1, wherein R is an aliphatic moiety selected from $C_1$-$C_{24}$ alkyl substituted with hydroxyl groups and $C_1$-$C_{24}$ alkenyl substituted with hydroxyl groups.

12. The method of claim 1, wherein R is an aliphatic moiety selected from $C_1$-$C_{24}$ alkyl substituted with carboxyl groups and $C_1$-$C_{24}$ alkenyl substituted with carboxyl groups.

13. The method of claim 1, wherein R is an aliphatic moiety selected from $C_1$-$C_{24}$ alkyl substituted with aromatic groups and $C_1$-$C_{24}$ alkenyl substituted with aromatic groups.

* * * * *